(12) United States Patent
Yee et al.

(10) Patent No.: US 10,568,759 B2
(45) Date of Patent: Feb. 25, 2020

(54) TREATMENT SYSTEMS, SMALL VOLUME APPLICATORS, AND METHODS FOR TREATING SUBMENTAL TISSUE

(71) Applicants: Peter Yee, San Ramon, CA (US); Joseph Coakley, Dublin, CA (US); George Frangineas, Jr., Fremont, CA (US); Tamara Hilton, Pleasanton, CA (US)

(72) Inventors: Peter Yee, San Ramon, CA (US); Joseph Coakley, Dublin, CA (US); George Frangineas, Jr., Fremont, CA (US); Tamara Hilton, Pleasanton, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 548 days.

(21) Appl. No.: 14/705,868

(22) Filed: May 6, 2015

(65) Prior Publication Data

US 2016/0051401 A1 Feb. 25, 2016

Related U.S. Application Data

(60) Provisional application No. 62/039,213, filed on Aug. 19, 2014.

(51) Int. Cl.
*A61F 7/02* (2006.01)
*A61F 7/00* (2006.01)

(52) U.S. Cl.
CPC ...... *A61F 7/007* (2013.01); *A61F 2007/0012* (2013.01); *A61F 2007/0056* (2013.01);
(Continued)

(58) Field of Classification Search
CPC ...... A61F 2007/0001; A61F 2007/0239; A61F 2007/0056
See application file for complete search history.

(56) References Cited

U.S. PATENT DOCUMENTS

| 681,806 A | 9/1901 | Mignault et al. |
| 889,810 A | 6/1908 | Robinson et al. |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.
(Continued)

*Primary Examiner* — Kaitlyn E Smith
*Assistant Examiner* — Yasamin Ekrami
(74) *Attorney, Agent, or Firm* — Perkins Coie LLP

(57) ABSTRACT

Systems for treating a subject's tissue can include a thermally conductive cup, a tissue-receiving cavity, and a vacuum port. The vacuum port is in fluid communication with the tissue-receiving cavity to provide a vacuum for drawing the submental tissue, or other targeted tissue, into the tissue-receiving cavity. A thermal device can cool and/or heat the conductive cup such that the conductive cup noninvasively controls the temperature of subcutaneous lipid-rich cells in the tissue. A restraint apparatus can hold a the conductive cup in thermal contact with the target region.

22 Claims, 22 Drawing Sheets

(52) U.S. Cl.
CPC ............... A61F 2007/0071 (2013.01); A61F 2007/0075 (2013.01); A61F 2007/0239 (2013.01)

(56) References Cited

U.S. PATENT DOCUMENTS

| | | | |
|---|---|---|---|
| 1,093,868 A | 4/1914 | Leighty | |
| 2,516,491 A | 7/1950 | Swastek | |
| 2,521,780 A * | 9/1950 | Dodd | A47G 9/1036 4/523 |
| 2,726,658 A | 12/1955 | Chessey | |
| 2,766,619 A | 10/1956 | Tribus et al. | |
| 2,851,602 A | 9/1958 | Cramwinckel et al. | |
| 3,093,135 A | 6/1963 | Hirschhorn | |
| 3,132,688 A | 5/1964 | Nowak | |
| 3,133,539 A | 5/1964 | Eidus et al. | |
| 3,282,267 A | 11/1966 | Eidus | |
| 3,502,080 A | 3/1970 | Hirschhorn | |
| 3,587,577 A | 6/1971 | Zubkov et al. | |
| 3,591,645 A | 7/1971 | Selwitz | |
| 3,692,338 A | 9/1972 | Nick | |
| 3,703,897 A | 11/1972 | Mack et al. | |
| 3,710,784 A | 1/1973 | Taylor | |
| 3,786,814 A | 1/1974 | Armao | |
| 3,827,436 A | 8/1974 | Andera et al. | |
| 3,942,519 A | 3/1976 | Shock | |
| 3,948,269 A | 4/1976 | Zimmer | |
| 3,986,385 A | 10/1976 | Johnston et al. | |
| 3,993,053 A | 11/1976 | Grossan | |
| 4,002,221 A | 1/1977 | Buchalter | |
| 4,026,299 A | 5/1977 | Sauder | |
| 4,140,130 A | 2/1979 | Storm | |
| 4,149,529 A | 4/1979 | Copeland et al. | |
| 4,178,429 A | 12/1979 | Scheffer | |
| 4,202,336 A | 5/1980 | Van Gerven | |
| 4,266,043 A | 5/1981 | Fujii et al. | |
| 4,269,068 A | 5/1981 | Molina | |
| 4,381,009 A | 4/1983 | Del Bon | |
| 4,396,011 A | 8/1983 | Mack et al. | |
| 4,459,854 A | 7/1984 | Richardson et al. | |
| 4,470,263 A | 9/1984 | Lehovec et al. | |
| 4,483,341 A | 11/1984 | Witteles | |
| 4,528,979 A | 7/1985 | Marchenko et al. | |
| 4,531,524 A | 7/1985 | Mioduski | |
| 4,548,212 A | 10/1985 | Leung | |
| 4,555,313 A | 11/1985 | Duchane et al. | |
| 4,585,002 A | 4/1986 | Kissin | |
| 4,603,076 A | 7/1986 | Bowditch et al. | |
| 4,614,191 A | 9/1986 | Perler et al. | |
| 4,644,955 A | 2/1987 | Mioduski | |
| 4,664,110 A | 5/1987 | Schanzlin | |
| 4,700,701 A | 10/1987 | Montaldi | |
| 4,718,429 A | 1/1988 | Smidt | |
| 4,741,338 A | 5/1988 | Miyamae | |
| 4,758,217 A | 7/1988 | Gueret | |
| 4,764,463 A | 8/1988 | Mason et al. | |
| 4,802,475 A | 2/1989 | Weshahy | |
| 4,832,022 A | 5/1989 | Tjulkov et al. | |
| 4,846,176 A | 7/1989 | Golden | |
| 4,850,340 A | 7/1989 | Onishi | |
| 4,869,250 A | 9/1989 | Bitterly | |
| 4,880,564 A | 11/1989 | Abel et al. | |
| 4,905,697 A | 3/1990 | Heggs et al. | |
| 4,906,463 A | 3/1990 | Cleary et al. | |
| 4,930,317 A | 6/1990 | Klein | |
| 4,935,345 A | 6/1990 | Guilbeau et al. | |
| 4,961,422 A | 10/1990 | Marchosky et al. | |
| 4,962,761 A | 10/1990 | Golden | |
| 4,990,144 A | 2/1991 | Blott et al. | |
| 5,007,433 A | 4/1991 | Hermsdoerffer et al. | |
| 5,018,521 A | 5/1991 | Campbell et al. | |
| 5,024,650 A | 6/1991 | Hagiwara et al. | |
| 5,065,752 A | 11/1991 | Sessions et al. | |
| 5,069,208 A | 12/1991 | Noppel et al. | |
| 5,084,671 A | 1/1992 | Miyata et al. | |
| 5,108,390 A | 4/1992 | Potocky et al. | |
| 5,119,674 A | 6/1992 | Nielsen | |
| 5,139,496 A | 8/1992 | Hed | |
| 5,143,063 A | 9/1992 | Fellner | |
| 5,148,804 A | 9/1992 | Hill et al. | |
| 5,158,070 A | 10/1992 | Dory | |
| 5,169,384 A | 12/1992 | Bosniak et al. | |
| 5,197,466 A | 3/1993 | Marchosky et al. | |
| 5,207,674 A | 5/1993 | Hamilton | |
| 5,221,726 A | 6/1993 | Dabi et al. | |
| 5,264,234 A | 11/1993 | Windhab et al. | |
| 5,277,030 A | 1/1994 | Miller | |
| 5,314,423 A | 5/1994 | Seney et al. | |
| 5,327,886 A | 7/1994 | Chiu | |
| 5,330,745 A | 7/1994 | Mcdow et al. | |
| 5,333,460 A | 8/1994 | Lewis et al. | |
| 5,334,131 A | 8/1994 | Omandam et al. | |
| 5,336,616 A | 8/1994 | Livesey et al. | |
| 5,339,541 A | 8/1994 | Owens | |
| 5,342,617 A | 8/1994 | Gold et al. | |
| 5,351,677 A | 10/1994 | Kami et al. | |
| 5,358,467 A | 10/1994 | Milstein et al. | |
| 5,362,966 A | 11/1994 | Rosenthal et al. | |
| 5,363,347 A | 11/1994 | Nguyen | |
| 5,372,608 A | 12/1994 | Johnson | |
| 5,386,837 A | 2/1995 | Sterzer | |
| 5,411,541 A | 5/1995 | Bell et al. | |
| 5,427,772 A | 6/1995 | Hagan et al. | |
| 5,433,717 A | 7/1995 | Rubinsky et al. | |
| 5,456,703 A | 10/1995 | Beeuwkes, III et al. | |
| 5,472,416 A | 12/1995 | Blugerman et al. | |
| 5,486,207 A | 1/1996 | Mahawili | |
| 5,497,596 A | 3/1996 | Zatkulak | |
| 5,501,655 A | 3/1996 | Rolt et al. | |
| 5,505,726 A | 4/1996 | Meserol | |
| 5,505,730 A | 4/1996 | Edwards et al. | |
| 5,507,790 A | 4/1996 | Weiss | |
| 5,514,105 A | 5/1996 | Goodman, Jr. et al. | |
| 5,514,170 A | 5/1996 | Mauch | |
| 5,516,505 A | 5/1996 | McDow | |
| 5,531,742 A | 7/1996 | Barken | |
| 5,562,604 A | 10/1996 | Yablon et al. | |
| 5,571,801 A | 11/1996 | Segall et al. | |
| 5,575,812 A | 11/1996 | Owens et al. | |
| 5,603,221 A | 2/1997 | Maytal | |
| 5,628,769 A | 5/1997 | Saringer | |
| 5,634,890 A | 6/1997 | Morris | |
| 5,634,940 A | 6/1997 | Panyard | |
| 5,647,051 A | 7/1997 | Neer | |
| 5,647,868 A | 7/1997 | Chinn | |
| 5,650,450 A | 7/1997 | Lovette et al. | |
| 5,651,773 A | 7/1997 | Perry et al. | |
| 5,654,279 A | 8/1997 | Rubinsky et al. | |
| 5,654,546 A | 8/1997 | Lindsay et al. | |
| 5,660,836 A | 8/1997 | Knowlton et al. | |
| 5,665,053 A | 9/1997 | Jacobs | |
| 5,672,172 A | 9/1997 | Zupkas | |
| 5,700,284 A | 12/1997 | Owens et al. | |
| 5,725,483 A | 3/1998 | Podolsky | |
| 5,733,280 A | 3/1998 | Avitall | |
| 5,741,248 A | 4/1998 | Stern et al. | |
| 5,746,702 A | 5/1998 | Gelfgat et al. | |
| 5,746,736 A | 5/1998 | Tankovich | |
| 5,755,663 A | 5/1998 | Larsen et al. | |
| 5,755,753 A | 5/1998 | Knowlton et al. | |
| 5,755,755 A | 5/1998 | Panyard | |
| 5,759,182 A | 6/1998 | Varney et al. | |
| 5,759,764 A | 6/1998 | Polovina et al. | |
| 5,769,879 A | 6/1998 | Richards et al. | |
| 5,785,955 A | 7/1998 | Fischer | |
| 5,792,080 A | 8/1998 | Ookawa et al. | |
| 5,800,490 A | 9/1998 | Patz et al. | |
| 5,814,040 A | 9/1998 | Nelson et al. | |
| 5,817,050 A | 10/1998 | Klein et al. | |
| 5,817,149 A | 10/1998 | Owens et al. | |
| 5,817,150 A | 10/1998 | Owens et al. | |
| 5,830,208 A | 11/1998 | Muller et al. | |
| 5,833,685 A | 11/1998 | Tortal et al. | |
| 5,844,013 A | 12/1998 | Kenndoff et al. | |

(56) References Cited

U.S. PATENT DOCUMENTS

| | | |
|---|---|---|
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A * | 11/2000 | Koby ............... A47G 9/1027 5/644 |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B2 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |

(56) References Cited

U.S. PATENT DOCUMENTS

| | | |
|---|---|---|
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1* | 4/2003 | Lurie .................. A61M 16/20 128/203.11 |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1* | 1/2005 | Lau .................. A61B 17/0206 606/1 |
| 2005/0033957 A1 | 2/2005 | Enokida |
| 2005/0049526 A1 | 3/2005 | Baer |

(56) References Cited

U.S. PATENT DOCUMENTS

| | | |
|---|---|---|
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1* | 3/2008 | Levinson .............. A61F 7/10 607/108 |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1* | 7/2008 | Mercuro .............. A61F 7/10 607/109 |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1* | 10/2008 | Deem .............. A61B 18/18 607/101 |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1* | 11/2010 | Baker .............. A61F 7/007 607/113 |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |

(56) References Cited

U.S. PATENT DOCUMENTS

| | | |
|---|---|---|
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1* | 9/2012 | Weber ............... A61F 7/02 607/104 |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1* | 10/2015 | Lee ............... A61F 7/007 601/2 |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'Neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |

FOREIGN PATENT DOCUMENTS

| | | |
|---|---|---|
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2779893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |

(56) References Cited

FOREIGN PATENT DOCUMENTS

| | | |
|---|---|---|
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

(56) References Cited

OTHER PUBLICATIONS

Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiological Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
International Search Report and Written Opinion for PCT/US2015/045714; Applicant: Zeltiq Aesthetics, Inc.; dated Jan. 13, 2016, 19 pages.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.

(56) References Cited

OTHER PUBLICATIONS

Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

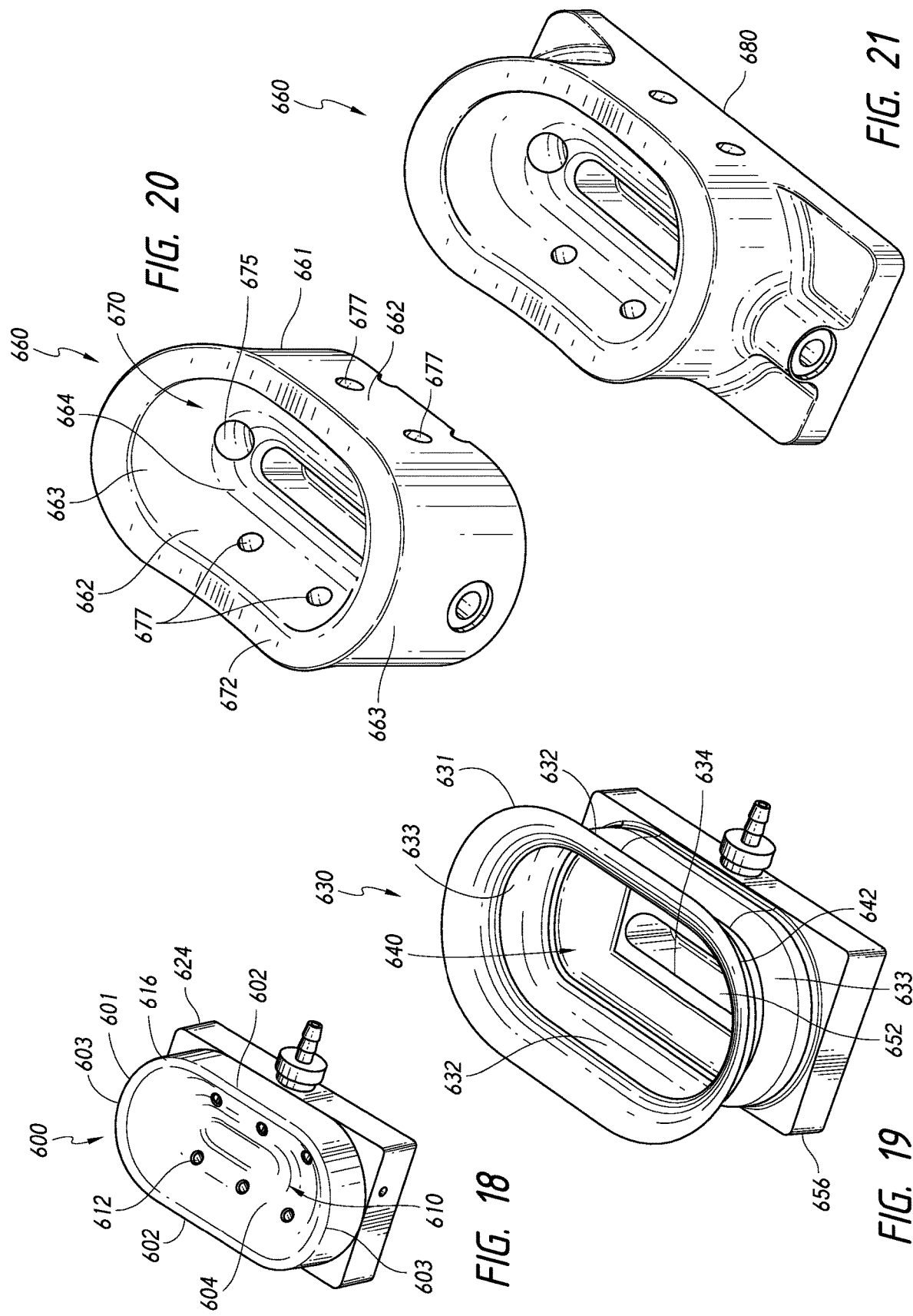

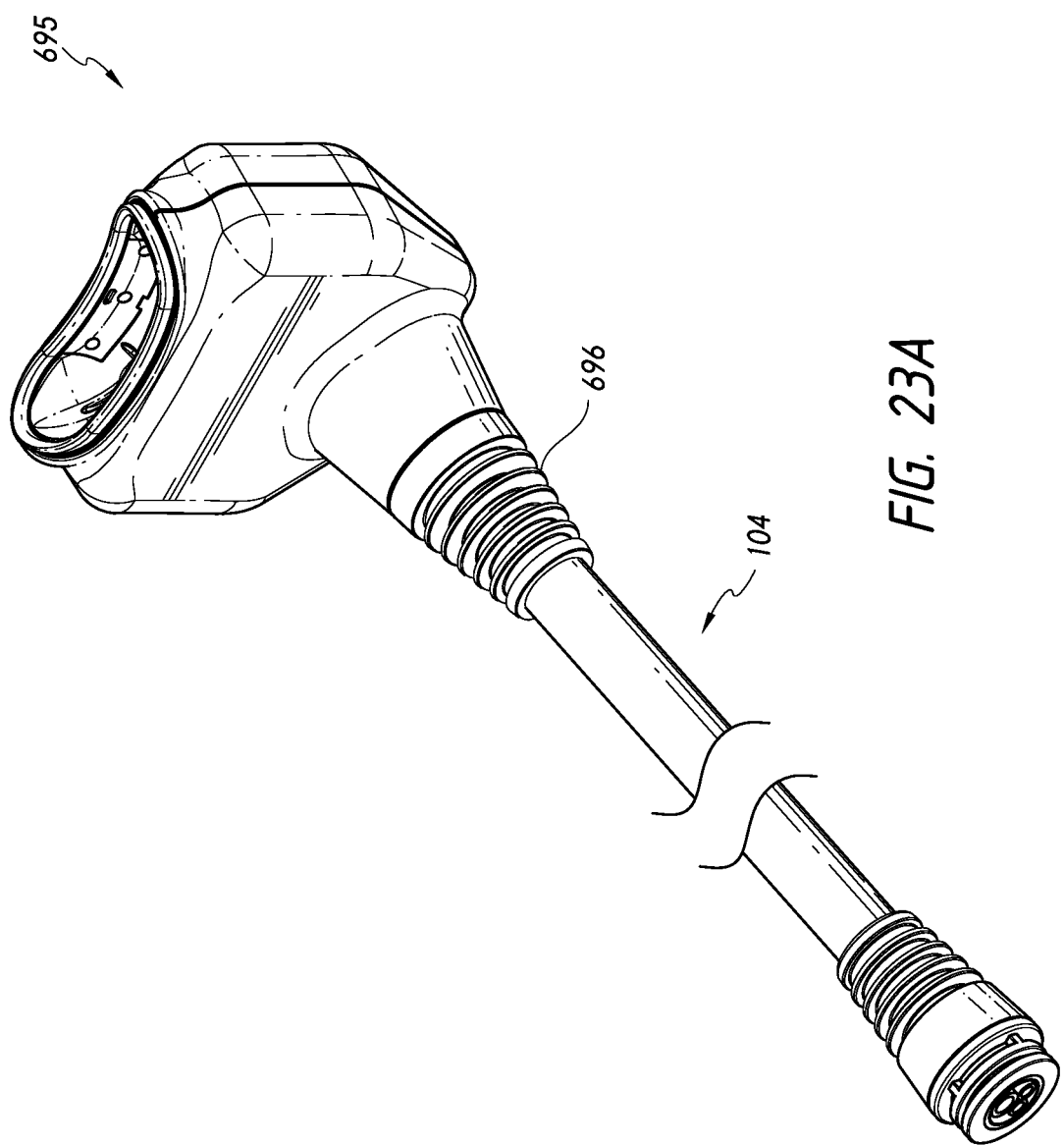

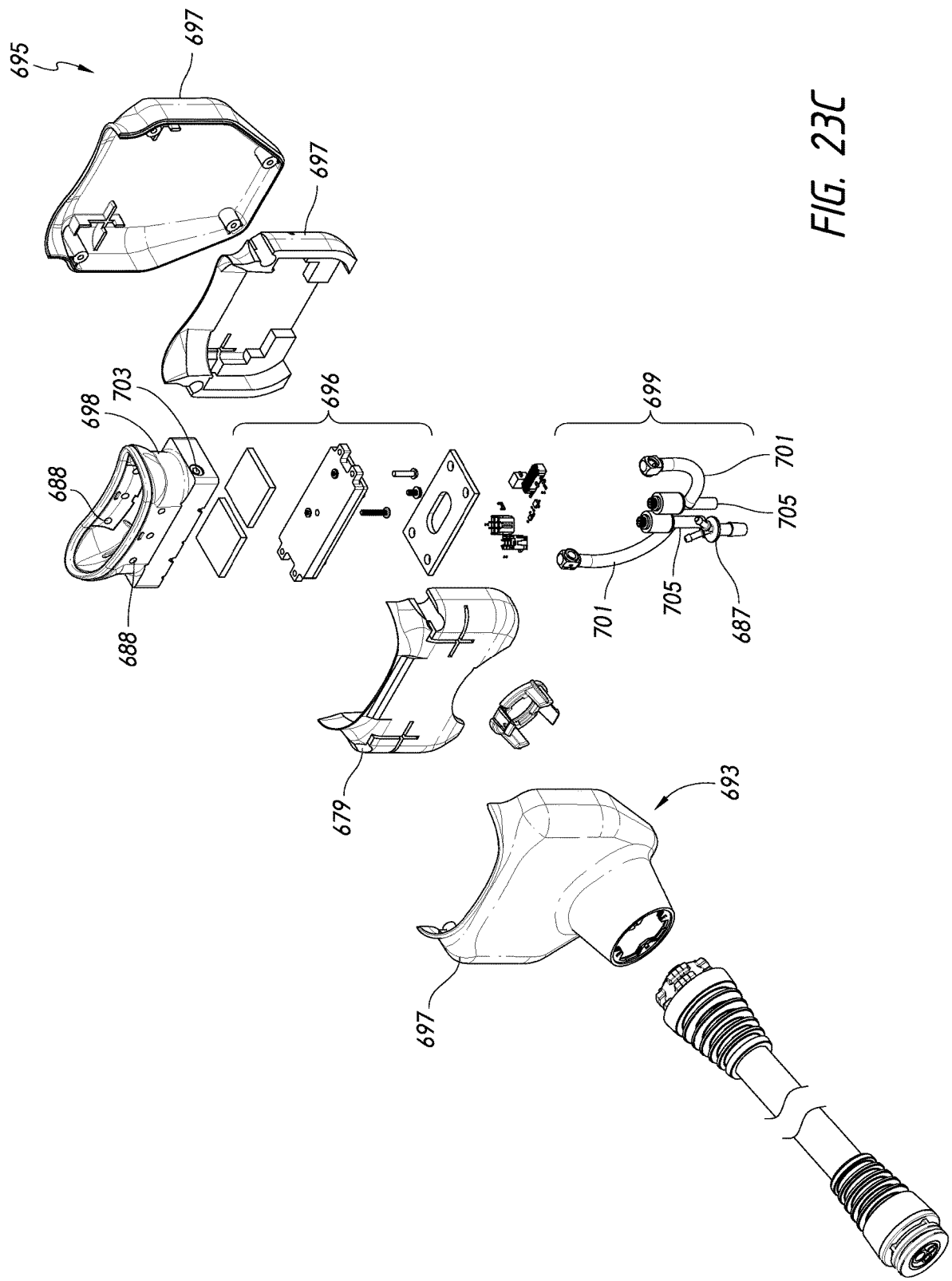

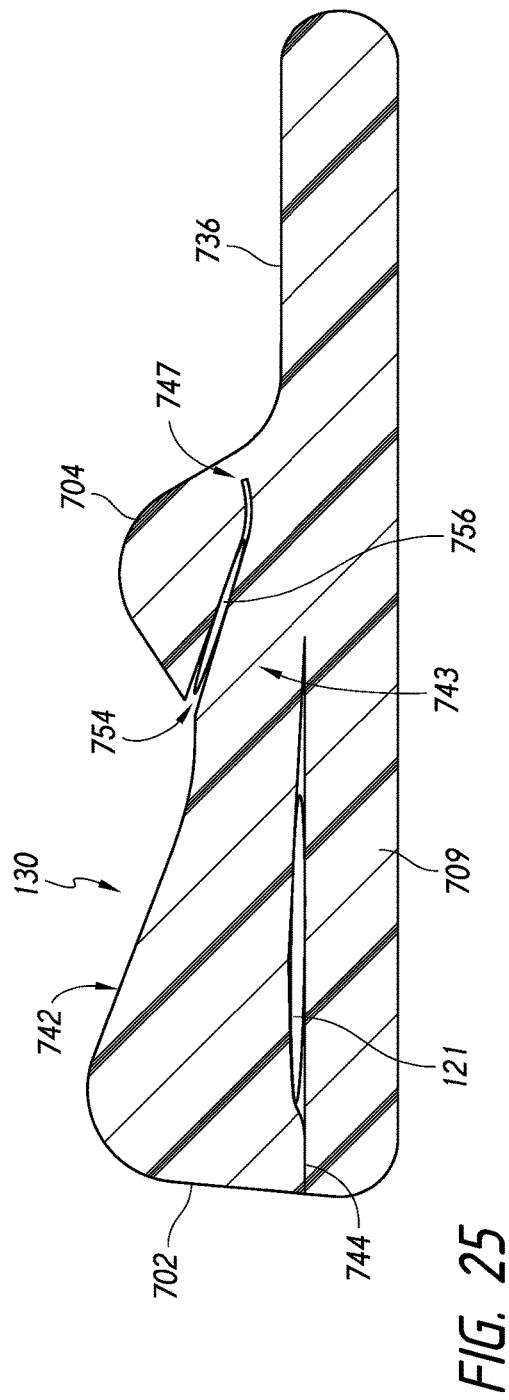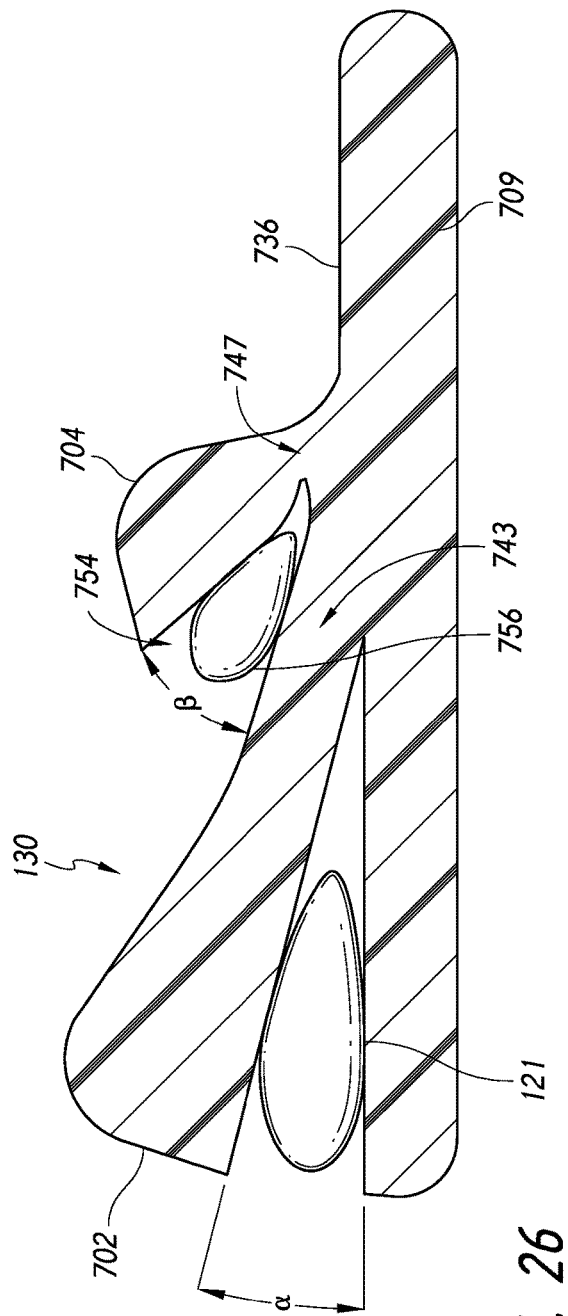

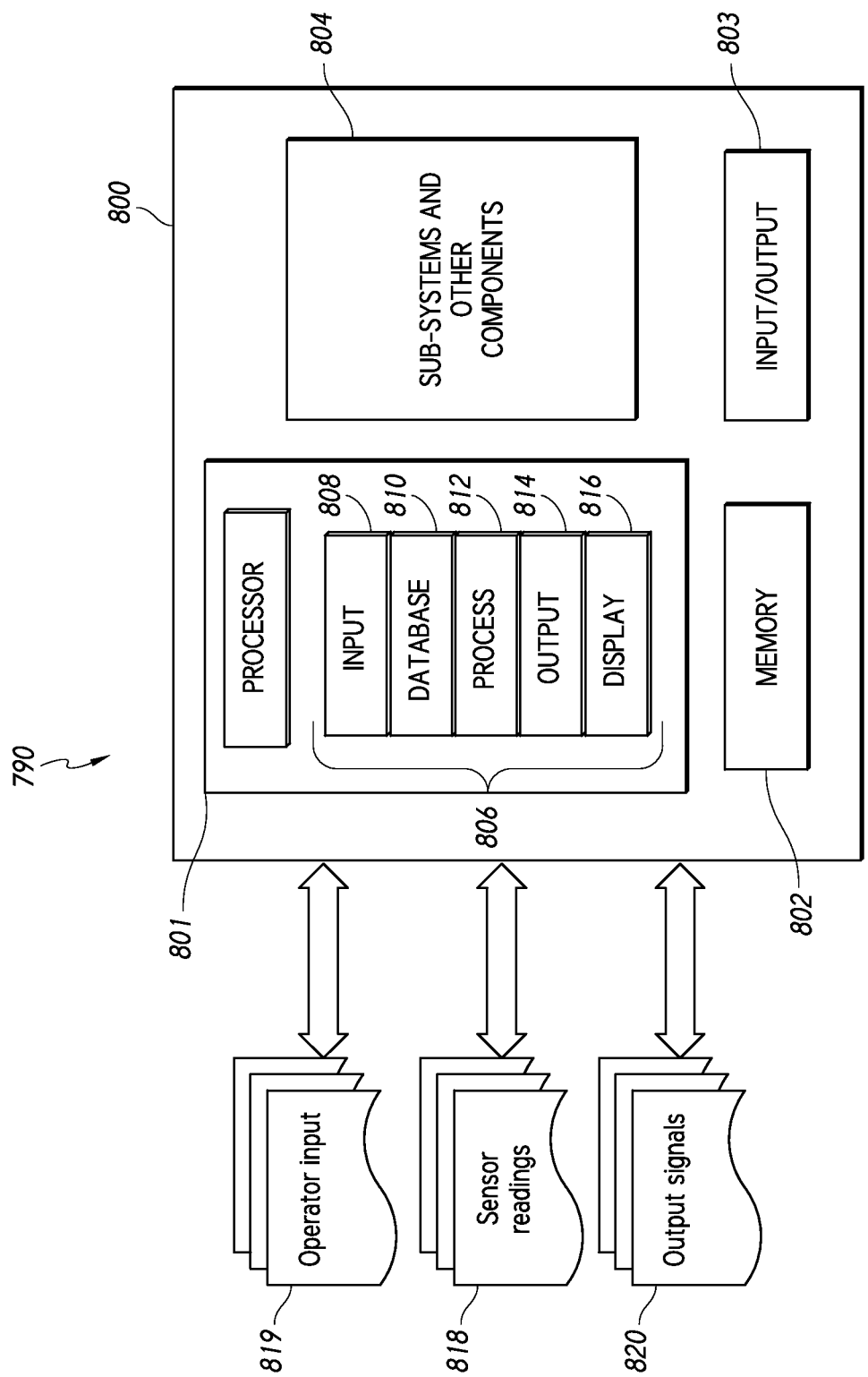

TREATMENT SYSTEMS, SMALL VOLUME APPLICATORS, AND METHODS FOR TREATING SUBMENTAL TISSUE

CROSS-REFERENCE TO RELATED APPLICATION

This application claims the benefit under 35 U.S.C. § 119(e) of U.S. Provisional Patent Application No. 62/039,213 filed Aug. 19, 2014, which is incorporated by reference in its entirety.

INCORPORATION BY REFERENCE OF COMMONLY-OWNED APPLICATIONS AND PATENTS

The following commonly assigned U.S. patent applications and U.S. patents are incorporated herein by reference in their entireties:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. patent application Ser. No. 13/830,413 entitled "MULTI-MODALITY TREATMENT SYSTEMS, METHODS AND APPARATUS FOR ALTERING SUBCUTANEOUS LIPID-RICH TISSUE";

U.S. patent application Ser. No. 13/830,027 entitled "TREATMENT SYSTEMS WITH FLUID MIXING SYSTEMS AND FLUID-COOLED APPLICATORS AND METHODS OF USING THE SAME";

U.S. patent application Ser. No. 11/528,225 entitled "COOLING DEVICE HAVING A PLURALITY OF CONTROLLABLE COOLING ELEMENTS TO PROVIDE A PREDETERMINED COOLING PROFILE;" and U.S. Pat. No. 8,285,390 entitled "MONITORING THE COOLING OF SUBCUTANEOUS LIPID-RICH CELLS, SUCH AS THE COOLING OF ADIPOSE TISSUE."

TECHNICAL FIELD

The present disclosure relates generally to treatment systems for cooling and/or cooling targeted regions. Several embodiments are directed to treatment systems with non-invasive applicators that hold and cool/heat relatively small volumes of tissue. Several embodiments can also include restraint apparatuses for holding non-invasive applicators in thermal contact with patients.

BACKGROUND

Excess body fat, or adipose tissue, may be present at various locations of a subject's body and may detract from personal appearance. Excess subcutaneous fat under the chin and/or around the neck can be cosmetically unappealing and, in some instances, can produce a "double chin." A double chin can cause stretching and/or sagging of skin and may also result in discomfort. Excess adipose tissue in superficial fat compartments can produce loose facial structures, such as loose jowls, that also cause an undesirable appearance. Excess body fat can also be located at the abdomen, thighs, buttocks, knees, and arms, as well as other locations.

Aesthetic improvement of the human body often involves the selective removal of adipose tissue. Invasive procedures (e.g., liposuction), however, tend to be associated with relative high costs, long recovery times, and increased risk of complications. Injection of drugs for reducing adipose tissue, such as submental or facial adipose tissue, can cause significant swelling, bruising, pain, numbness, and/or induration. Conventional non-invasive treatments for reducing adipose tissue often include regular exercise, application of topical agents, use of weight-loss drugs, dieting, or a combination of these treatments. One drawback of these non-invasive treatments is that they may not be effective or even possible under certain circumstances. For example, when a person is physically injured or ill, regular exercise may not be an option. Topical agents and orally administered weight-loss drugs are not an option if, as another example, they cause an undesirable reaction (e.g., an allergic or negative reaction). Additionally, non-invasive treatments may be ineffective for selectively reducing specific regions of adiposity. For example, localized fat loss around the neck, jaw, cheeks, etc. often cannot be achieved using general or systemic weight-loss methods. Accordingly, conventional invasive and non-invasive treatments are not suitable for many subjects and cannot effectively target certain regions of adipose tissue.

SUMMARY OF TECHNOLOGY

Systems for treating a subject's tissue can include a thermally conductive cup, a tissue-receiving cavity, and a vacuum port. The vacuum port can be in fluid communication with the tissue-receiving cavity to provide a vacuum for drawing the submental tissue, or other targeted tissue, into the tissue-receiving cavity. The system can cool and/or heat the conductive cup such that the conductive cup non-invasively controls the temperature of subcutaneous lipid-rich cells in the tissue. A restraint apparatus can hold the thermally conductive cup in thermal contact with a patient's tissue.

At least some embodiments are apparatuses for treating a subject's submental tissue and can include a thermally conductive cup, at least one vacuum port, and a thermal device. The thermally conductive cup can include a first sidewall, a second sidewall, and a bottom. The vacuum port can be in fluid communication with a tissue-receiving cavity of the cup to provide a vacuum for drawing the submental tissue into the tissue-receiving cavity. The tissue-receiving cavity can be sufficiently shallow to allow the subject's submental tissue to occupy substantially the entire tissue-receiving cavity when the vacuum is drawn via the vacuum port. The thermal device can be in thermal communication with the conductive cup. The thermal device can be configured to cool the conductive cup such that the first sidewall, second sidewall, and bottom together non-invasively cool subcutaneous lipid-rich cells in the submental tissue. For example, the subcutaneous lipid-rich cells can be cooled an amount sufficient to be biologically effective in damaging and/or reducing the subcutaneous lipid-rich cells or other targeted cells.

The first sidewall, second sidewall, and bottom can be positioned to absorb heat from the submental tissue to damage and/or reduce the lipid-rich cells, which are in a subcutaneous layer of adipose tissue, in number and/or size to an extent while non-lipid-rich cells deeper than the subcutaneous layer of adipose tissue are not reduced in number and/or size to the extent. In some embodiments, the apparatus can include a pressurization device in fluid communication with the tissue-receiving cavity via the vacuum port. A controller can include instructions for causing the apparatus to hold the submental tissue in the tissue-receiving cavity using suction provided by the pressurization device.

The conductive cup can be in thermal contact with most of the subject's skin at the subject's submental region when the tissue-receiving cavity is partially or completely filled with the subject's tissue. The conductive cup can include a conductive surface (e.g., metal surface) that faces the tissue-receiving cavity and has an area equal to or less than about, for example, 40 cm². In some embodiments, the conductive cup can include a smooth thermally conductive surface that extends continuously along the first sidewall, second sidewall, and bottom.

The tissue-receiving cavity can be dimensioned to receive most of the subject's skin located at the submental region of the subject. In some embodiments, the tissue-receiving cavity has a length between opposing end walls of the conductive cup, a width between the first and second sidewalls, and a depth between an opening of the tissue-receiving cavity and the bottom of the conductive cup. The depth is substantially uniform along most of the length of the tissue-receiving cavity.

A liner assembly can line the conductive cup such that the liner assembly is positioned between the subject's tissue in the tissue-receiving cavity and the conductive cup. The linear assembly can be made of plastic, rubber, or other suitable material and can carry and/or include one or more sensors.

In some embodiments, an apparatus for treating a subject's tissue includes a submental vacuum applicator. The submental vacuum applicator can include a tissue-receiving cavity, a contoured lip, and a thermal device. The contoured lip can define a mouth of the tissue-receiving cavity and can include first and second arcuate lip portions. The contoured lip can be configured to engage a submental area of the subject such that mostly submental tissue extends through the mouth and fills substantially all of the tissue-receiving cavity while the submental vacuum applicator draws a vacuum and the first and second arcuate lip portions surround at least a portion of the subject's body. The thermal device can be positioned to be in thermal contact with the submental tissue in the tissue-receiving cavity. The thermal device is operable to non-invasively cool subcutaneous lipid-rich cells in the submental tissue an amount sufficient to be biologically effective in damaging, reducing, and/or otherwise affecting the subcutaneous lipid-rich cells.

The apparatus can include a controller with instructions for causing the submental vacuum applicator to cool a conductive cup such that the submental vacuum applicator non-invasively cools the subcutaneous lipid-rich cells to a temperature less than about predetermined temperature (e.g., about 0° C., about −1.8° C., etc.). The controller can include one or more processors, memory, power supplies, or other electrical components.

The tissue-receiving cavity can include a first end, a second end, and a central section extending between the first and second ends. The central section has a curved longitudinal axis and a substantially uniform maximum depth along most of the curved longitudinal axis. In one embodiment, the curved longitudinal axis has the same curvature as a curvature of at least one of the first and second arcuate lip portions. In one embodiment, the tissue-receiving cavity has a substantially uniform maximum depth along most of a longitudinal length of the tissue-receiving cavity.

The apparatus can further include a vacuum source fluidically coupled to the tissue-receiving cavity. The vacuum source can be configured to provide sufficient vacuum to draw the submental tissue toward a bottom of the tissue-receiving cavity to bring the submental tissue into thermal contact with a concave metal heat-exchanging surface of the submental vacuum applicator.

The submental vacuum applicator, in some embodiments, can include an applicator unit and a liner assembly removably attached to the applicator unit. In other embodiments, the applicator unit can be used without any liner assembly.

In further embodiments, a method of non-invasively cooling a submental region of a subject includes placing a submentum applicator on the subject. The submentum applicator includes a vacuum cup and a tissue-receiving cavity. Submental tissue can be drawn through the tissue-receiving cavity and into thermal contact with a section of the vacuum cup located at a bottom of the tissue-receiving cavity. Heat can be conductively extracted from the submental tissue by the submentum applicator so as to cool the submental tissue an amount sufficient to be biologically effective in selectively damaging and/or reducing subcutaneous submental lipid-rich cells. Heat can be repeatedly extracted from the subcutaneous submental tissue until desired tissue reduction is achieved. In some embodiments, a sufficient amount of heat can be conductively extracted from the submental tissue to visibly reduce a double chin of the subject.

The conductive extraction of heat can include conductively cooling an area of the subject's submental skin that is equal to or less than about 40 $cm^2$. In some embodiments, a concave heat-exchanging surface of the applicator can be cooled to a temperature equal to or less than a selected temperature (e.g., 0° C.). In some embodiments, most of a heat-exchanging surface of a conductive cup of the vacuum applicator can be cooled to a temperature equal to or less than about −5° C. The submental tissue can be pulled into the tissue-receiving cavity such that the tissue-receiving cavity is filled mostly with submental tissue. In some embodiments, a vacuum can be drawn to pull the submental tissue into the tissue-receiving cavity and can result in a relatively large contact area for heat transfer with the target tissue.

In some embodiments, a system includes a restraint apparatus configured to hold a subject's head. The restraint apparatus can include an adjustable pillow and restraints. The pillow can include a head cradle portion operable to controllably adjust tilt of a subject's head. The restraints are coupleable to the pillow such that the restraints hold a tissue-cooling apparatus in thermal contact with the subject's submental region while the subject's head is supported at a desired tilt by the head cradle portion.

The system can further include a tissue-cooling apparatus configured to be connected to the pillow by the restraints. The restraints and pillow cooperate to inhibit movement of the tissue-cooling apparatus relative to the subject's submental region while the tissue-cooling apparatus non-invasively cools subcutaneous lipid-rich cells at the subject's submental region. For example, the subcutaneous lipid-rich cells can be cooled an amount sufficient to be biologically effective in damaging and/or reducing the subcutaneous lipid-rich cells. In some embodiments, the pillow and restraints can be configured to cooperate to inhibit movement of the subject's head while the tissue-cooling apparatus transcutaneously cools the subject's submental region.

The restraint apparatus, in some embodiments, further includes a head adjuster device and a neck adjuster device for reconfiguring the pillow. The head adjuster device is operable to reconfigure the head cradle portion of the pillow to achieve the desired tilt of the subject's head. The neck adjuster device is operable to reconfigure a neck support portion of the pillow to achieve desired neck tilt. In one embodiment, the head adjuster device has a bladder that expands to increase a slope of a tilted support surface of the head cradle portion so as to tilt the subject's head forward. In another embodiment, the head adjuster device includes a bladder located within an expandable opening of the pillow. The bladder can be inflated to expand at least a portion of the pillow to adjust head tilt of the subject.

The pillow, in some embodiments, can include a neck support portion which is positioned to be located under the subject's neck when the subject's head is supported by the head cradle portion. A neck adjuster device is operable to move the neck support portion against the subject's neck to adjust neck tilt of the subject. In some embodiments, the pillow includes side portions positionable on opposite sides of the subject's head. The restraint apparatus can be configured to extend across at least a portion of the subject's body to hold the tissue-cooling apparatus in thermal contact with the subject's submental region. The pillow can include a shoulder support portion and a neck support portion positioned between the shoulder support portion and the head cradle portion. The neck support portion can be moved relative to the shoulder support portion and/or head cradle portion to push against the posterior region of the subject's neck.

The restraint apparatus, in some embodiments, can include a cradle adjuster device and a neck adjuster device. The cradle adjuster device can have a first expandable element that can expand a sufficient amount to increase forward tilt of the subject's head. The neck adjuster device can have a second expandable element that can expand so as to cause the neck support portion to push against the subject's neck (e.g., a posterior region of the subject's neck) when the posterior region of the subject's head rests on the head cradle portion. The first and second expandable elements can be independently expanded to independently move different regions of the pillow.

In some embodiments, a system configured to position a subject's body includes an adjustable pillow configured to support the subject's head. The pillow can include a head cradle, a head adjuster device, and a neck adjuster device. The head cradle has side portions positioned to contact opposite sides of a subject's head received by the head cradle to inhibit movement of the subject's head. The head adjuster device is operable to tilt the head cradle portion to achieve desired tilt of the subject's head. The neck adjuster device is operable to reconfigure a neck support portion of the pillow such that the neck support portion pushes against the subject's neck to achieve desired neck tilt.

The system can further include one or more restraints configured to hold a tissue-cooling apparatus in thermal contact with the subject's submental region while the head cradle inhibits movement of the subject's head relative to the tissue-cooling apparatus. In one embodiment, the restraints have an open configuration for allowing the subject's head to be moved into or out of the head cradle and a closed configuration for keeping the subject's head in the head cradle. In some embodiments, the restraints can be tensioned to pull the tissue-cooling apparatus toward the subject's submental region. The restraint apparatus can include hook and loop fastener that detachably couples the restraints to the pillow. For example, the loop fastener can be part of or attached to the pillow. The hook fastener can be part of or attached to the restraints. In other embodiments, the system can include a harness, straps, fasteners (e.g., buckles, snaps, etc.), and/or other coupling means for holding the subject's body, tissue-cooling apparatus, or the like.

The system, in some embodiments, further includes a tissue-cooling apparatus and at least one restraint. The tissue-cooling apparatus is configured to non-invasively cool subcutaneous lipid-rich cells at the subject's submental region an amount sufficient to be biologically effective in damaging and/or reducing the subcutaneous lipid-rich cells. The restraint is detachably coupleable to the pillow and detachably coupleable to the tissue-cooling apparatus. The tissue-cooling apparatus can be a handheld device with one or more thermoelectric cooling devices (e.g., Peltier devices), cooling channels, sensors, electrical components (e.g., circuitry, controllers, etc.), and/or other components.

At least some treatment systems disclosed herein can include a restraint apparatus that includes an adjustable pillow and means for stabilizing a tissue-cooling apparatus. In some embodiments, the means for stabilizing the tissue-cooling apparatus can include one or more restraints. The pillow can include a head cradle portion and means for controllably adjusting tilt of the subject's head and/or neck supported by the adjustable pillow. In one embodiment, the means for controllably adjusting tilt of the subject's head and/or neck includes a bladder insertable into the adjustable pillow and a pump connected to the bladder. In one embodiment, the means for controllably adjusting tilt of the subject's head and/or neck includes a cradle adjuster device and a neck adjuster device. The cradle adjuster device is positionable in the head cradle portion and can be expanded to increase forward tilt of the subject's head. The neck adjuster device can be expanded to cause a neck support portion of the pillow to push against the subject's neck when the subject's head is supported by the head cradle portion.

The head cradle portion, in some embodiments, can include side portions spaced apart to be positioned on opposite sides of the subject's head. The means for stabilizing the tissue-cooling apparatus can include restraints connectable to the side portions such that the one or more of the restraints extend across the subject's body to hold the tissue-cooling apparatus in thermal contact with the subject's submental region. In some embodiments, the means for stabilizing the tissue-cooling apparatus includes a retention system with one or more restraints, straps, or other coupling features.

BRIEF DESCRIPTION OF THE DRAWINGS

In the drawings, identical reference numbers identify similar elements or acts.

FIGS. 18-21 are isometric views of vacuum cups in accordance with embodiments of the present technology.

FIG. 23A is an isometric view of an applicator in accordance with embodiments of the technology.

FIG. 23C is an exploded isometric view of the applicator and connector of FIG. 23A in accordance with embodiments of the technology.

FIG. 25 is a cross-sectional view of the head support assembly taken along line 25-25 of FIG. 27 when a pillow is in an unexpanded lowered configuration.

FIG. 26 is a cross-sectional view of the head support assembly taken along line 26-26 of FIG. 27 when the pillow is in an expanded raised configuration.

FIG. 35 is a schematic block diagram illustrating subcomponents of a controller in accordance with embodiments of the technology.

DETAILED DESCRIPTION

A. Overview

Figure 1:
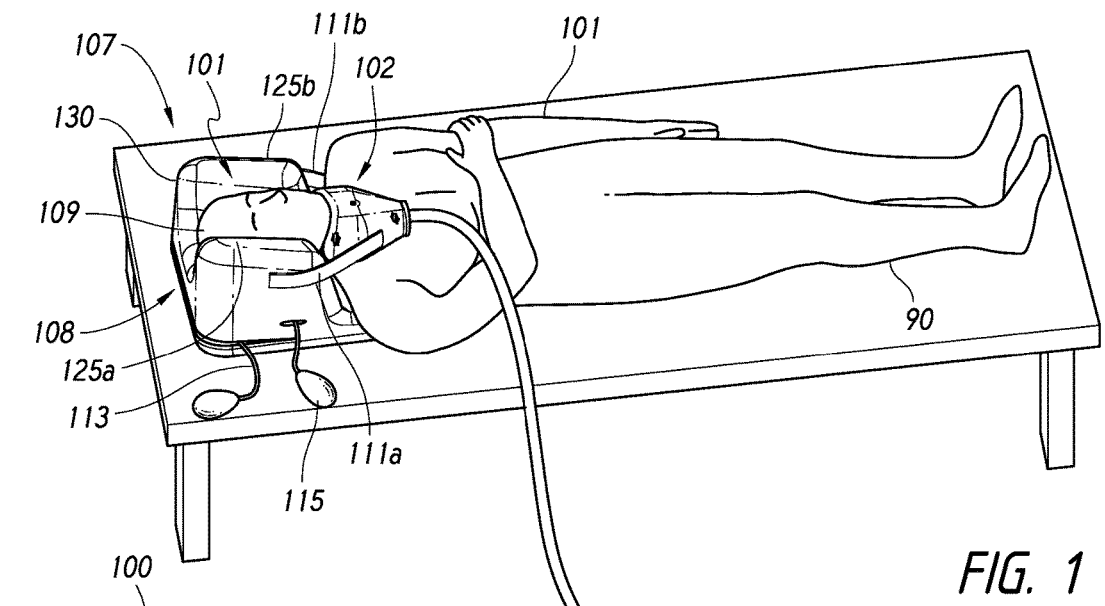
FIG. 1 is a partially schematic, isometric view of a treatment system for non-invasively affecting target regions of a subject in accordance with an embodiment of the technology.

The present disclosure describes treatment systems, applicators, and methods for affecting targeted sites. Several embodiments are directed to non-invasive systems that cool/heat relatively small regions or volumes of tissue, including submental tissue, neck tissue, etc. The systems can help position the patient's body to enhance treatment. Several of the details set forth below are provided to describe the following examples and methods in a manner sufficient to enable a person skilled in the relevant art to practice, make, and use them. Several of the details and advantages described below, however, may not be necessary to practice certain examples and methods of the technology. Additionally, the technology may include other examples and methods that are within the scope of the technology but are not described in detail.

At least some embodiments are systems for treating a subject's tissue and can include a thermally conductive cup, a tissue-receiving cavity, and a vacuum port. The vacuum port is in fluid communication with the tissue-receiving cavity to provide a vacuum for drawing the submental tissue into the tissue-receiving cavity. The thermal device can cool or heat the conductive cup such that the conductive cup non-invasively cools subcutaneous lipid-rich cells in the submental tissue an amount sufficient to affect targeted tissue. A restraint system can hold the conductive cup at the treatment site to enhance treatment.

In some embodiments, an apparatus for treating a subject's tissue includes a thermally conductive element, a vacuum port, and a thermal device for heating/cooling the conductive element. The conductive element can be a metal cup with sidewalls and a bottom. The vacuum port can be in fluid communication with a tissue-receiving cavity defined by the metal cup to provide a vacuum for drawing tissue into the tissue-receiving cavity. When the thermal device heats or cools the conductive cup, the heated/cooled sidewalls and/or bottom can non-invasively heat/cool subcutaneous lipid-rich cells in the submental tissue, which is located in the tissue-receiving cavity, an amount sufficient to be biologically effective in altering the subcutaneous lipid-rich cells. The thermal device can include one or more cooling/heating elements (e.g., resistive heaters, fluid-cooled elements, Peltier devices, etc.), controllers, sensors, or combinations thereof.

The term "treatment system", as used generally herein, refers to cosmetic or medical treatment systems, as well as any treatment regimens or medical device usage. Several embodiments of treatment system disclosed herein can reduce or eliminate excess adipose tissue or other undesirable tissue treatable using cryotherapy. The treatment systems can be used at various locations, including, for example, a subject's face, neck, abdomen, thighs, buttocks, knees, back, arms, ankles, and other areas. For example, a submental region can be treated to visibly reduce or eliminate a double chin or other unwanted tissue.

Some of the embodiments disclosed herein can be for cosmetically beneficial alterations of target regions. Some cosmetic procedures may be for the sole purpose of altering the target region to conform to a cosmetically desirable look, feel, size, shape and/or other desirable cosmetic characteristic or feature. Accordingly, at least some embodiments of the cosmetic procedures can be performed without providing an appreciable therapeutic effect (e.g., no therapeutic effect). For example, some cosmetic procedures may not include restoration of health, physical integrity, or the physical well-being of a subject. The cosmetic methods can target subcutaneous regions to change a subject's appearance and can include, for example, procedures performed on subject's submental region, face, neck, ankle region, or the like. In other embodiments, however, cosmetically desirable treatments may have therapeutic outcomes (whether intended or not), such as psychological benefits, alteration of body hormones levels (by the reduction of adipose tissue), etc.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology.

B. Cryotherapy

FIG. 1 and the following discussion provide a brief, general description of a treatment system 100 in accordance with some embodiments of the technology. The treatment system 100 can be a temperature-controlled system for exchanging heat with a subject 101 and can include a non-invasive tissue-cooling apparatus in the form of an applicator 102 ("applicator 102") configured to selectively cool/heat tissue to reduce and/or eliminate targeted tissue to achieve a desired overall appearance. The illustrated treatment system 100 includes a restraint apparatus 107 configured to hold the applicator 102 generally under the subject's chin to reduce or eliminate submental lipid-rich fat cells so as to reduce or eliminate, for example, a double chin. Skin, muscle, connective tissue of the neck and/or face, or other non-targeted tissue can be generally unaffected. The applicator 102 can also treat relatively small volumes of tissue at other locations.

The treatment system 100 can perform medical treatments to provide therapeutic effects and/or cosmetic procedures for cosmetically beneficial effect. Without being bound by theory, the selective effect of cooling is believed to result in, for example, membrane disruption, cell shrinkage, disabling, disrupting, damaging, destroying, removing, killing and/or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling can be the selectively reduction of lipid-rich cells by a desired mechanism of action, such as apoptosis, lipolysis, or the like. In some procedures, the applicator 102 can cool the tissue of the subject 101 to a temperature in a range of from about −25° C. to about 20° C. In other embodiments, the cooling temperatures can be from about −20° C. to about 10° C., from about −18° C. to about 5° C., from about −15° C. to about 5° C., or from about −15° C. to about 0° C. In further embodiments, the cooling temperatures can be equal to or less than −5° C., −10° C., −15° C., or in yet another embodiment, from about −15° C. to about −25° C. Other cooling temperatures and temperature ranges can be used.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relate to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation as a result of applied pressure, cooling which may affect vasoconstriction in the cooled tissue, or the like. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic, or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

One expected advantage of the foregoing techniques is that the subcutaneous lipid-rich cells in the target region can be reduced generally without collateral damage to non-lipid-rich cells in the same region. In general, lipid-rich cells can be affected at low temperatures that do not affect non-lipid-rich cells. As a result, lipid-rich cells, such as those associated with highly localized adiposity (e.g., submental adiposity, submandibular adiposity, facial adiposity, etc.), can be affected while non-lipid-rich cells (e.g., myocytes) in the same generally region are not damaged. The unaffected non-lipid-rich cells can be located underneath lipid-rich cells (e.g., cells deeper than a subcutaneous layer of fat), in the dermis, in the epidermis, and/or at other locations.

In some procedures, the treatment system 100 can remove heat from underlying tissue through the upper layers of tissue and create a thermal gradient with the coldest temperatures near the cooling surface, or surfaces, of the applicator 102 (i.e., the temperature of the upper layer(s) of the skin can be lower than that of the targeted underlying target cells). It may be challenging to reduce the temperature of the targeted cells low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., approximately, 5° C. to about 10° C., less than 10° C., less than 15° C., etc.). Protection of the overlying cells (e.g., typically water-rich dermal and epidermal skin cells) from freeze damage during dermatological and related aesthetic procedures that involve sustained exposure to cold temperatures may include improving the freeze tolerance and/or freeze avoidance of these skin cells by using, for example, cryoprotectants for inhibiting or preventing such freeze damage.

C. Treatment Systems

FIG. 1 shows the treatment system 100 that can include the applicator 102, the restraint apparatus 107, a connector 104, and a control module 106 for controlling operation of the applicator 102. The applicator 102 can conform closely to the contours of the subject's body. The restraint apparatus 107 can include a head support assembly 108 for holding the subject's head 109 and restraints 111a, 111b (collectively "restraints 111") for connecting the applicator 102 to the head support assembly 108. The head support assembly 108 can include an adjustable pillow 130 with independently movable features capable of positioning different regions of the subject's body any number of times. After completing a cryotherapy procedure, the restraints 111 can be detached from the pillow 130 to release the subject 101.

FIG. 1 shows the head support assembly 108 holding the subject's head 109 at a preferred position for treating submental tissue, reducing the likelihood of unintentional movement of the applicator 102 relative to the treatment site, to enhance a treatment. In some embodiments, the head support assembly 108 can include a head adjuster device 113 and a neck adjuster device 115. The head adjuster device 113 can be operated to adjust the forward tilt of the subject's head 109, and the neck adjuster device 115 can be operated to adjust the position of the subject's neck. The restraints 111 can be tensioned to pull the applicator 102 toward the subject's submental region and hold the subject's shoulders against side portions 125a, 125b (collectively "side portions 125"). The restraints 111 can be sufficiently tensioned to inhibit movement of the applicator 102 relative to the treatment site while the applicator 102 non-invasively cools the treatment site.

Figure 2:
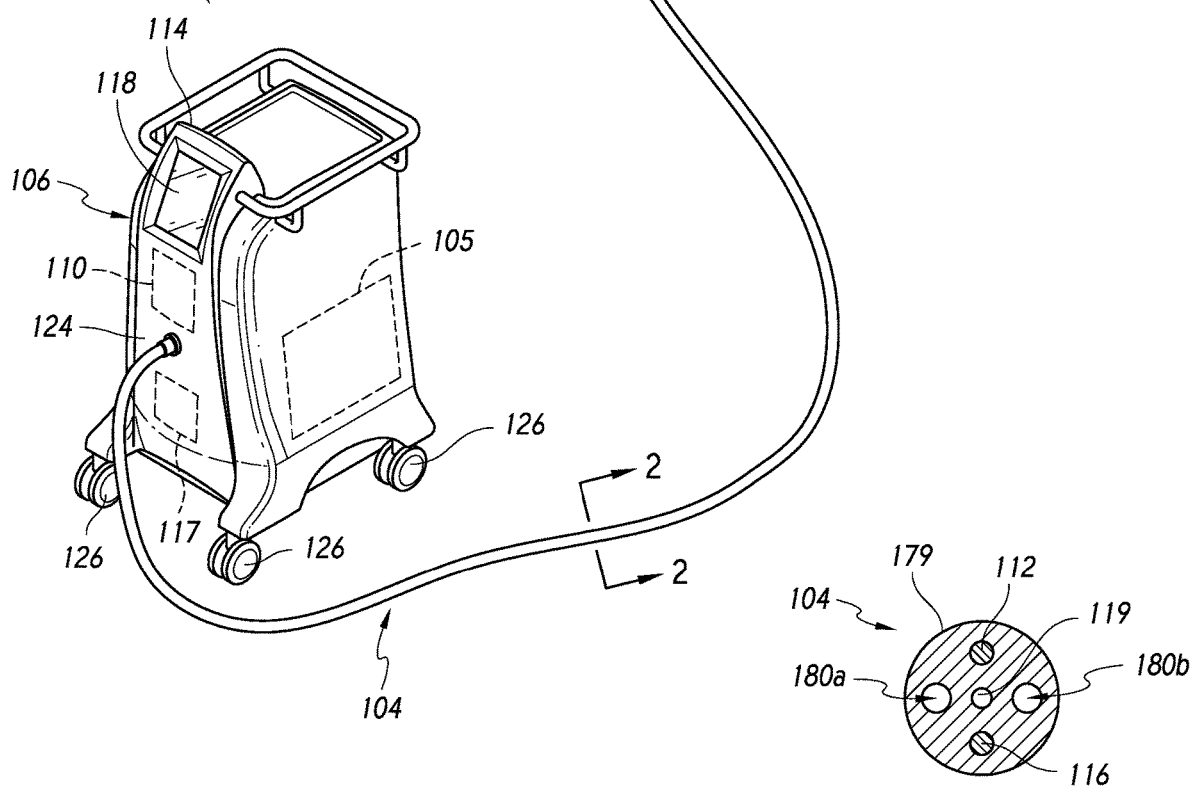
FIG. 2 is a cross-sectional view of a connector taken along line 2-2 of FIG. 1.

The connector 104 extends from the control module 106 to the applicator 102. FIG. 2 is a cross-sectional view of the connector 104 taken along line 2-2 of FIG. 1. Referring to FIG. 1, the connector 104 can provide suction for drawing tissue into the applicator 102 and energy (e.g., electrical energy) and fluid (e.g., coolant) from the control module 106 to the applicator 102. Referring now to FIG. 2, the connector 104 can include a main body 179, a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject 101. The supply and return fluid lines 180a, 180b can be conduits comprising, in whole or in part, polyethylene, polyvinyl chloride, polyurethane, and/or other materials that can accommodate circulating coolant, such as water, glycol, synthetic heat transfer fluid, oil, a refrigerant, and/or any other suitable heat conducting fluid. In one embodiment, each fluid line 180a, 180b can be a flexible hose surrounded by the main body 179. The connector 104 can also include one or more electrical lines 112 for providing power to the applicator 102 and one or more control lines 116 for providing communication between the control module 106 (FIG. 1) and the applicator 102 (FIG. 1). To provide suction, the connector 104 can include one or more vacuum lines 119. In various embodiments, the connector 104 can include a bundle of fluid conduits, a bundle of power lines, wired connections, vacuum lines, and other bundled and/or unbundled components selected to provide ergonomic comfort, minimize unwanted motion (and thus potential inefficient removal of heat from the subject 101), and/or to provide an aesthetic appearance to the treatment system 100.

Referring again to FIG. 1, the control module 106 can include a fluid system 105 (illustrated in phantom line), a power supply 110 (illustrated in phantom line), and a controller 114 carried by a housing 124 with wheels 126. The fluid system 105 can include a fluid chamber and a refrigeration unit, a cooling tower, a thermoelectric chiller, heaters, or any other device capable of controlling the temperature of coolant in the fluid chamber. The coolant can be continuously or intermittently delivered to the applicator 102 via the supply fluid line 180a (FIG. 2) and can circulate through the applicator 102 to absorb heat. The coolant, which has absorbed heat, can flow from the applicator 102 back to the control module 106 via the return fluid line 180b (FIG. 2). For warming periods, the control module 106 can heat the coolant such that warm coolant is circulated through the applicator 102. Alternatively, a municipal water supply (e.g., tap water) can be used in place of or in conjunction with the control module 106.

A pressurization device 117 can provide suction to the applicator 102 via the vacuum line 119 (FIG. 2) and can include one or more pumps, vacuum sources, or the like. Air pressure can be controlled by a regulator located between the pressurization device 117 and the applicator 102. If the vacuum level is too low, tissue may not be drawn adequately (or at all) into the applicator 102. If the vacuum level is too high, undesirable discomfort to the patient 101 and/or tissue damage could occur. The control module 106 can control the vacuum level to draw tissue into the applicator 102 while maintaining a desired level of comfort. According to certain embodiments, approximately 0.5 inch Hg, 1 inch Hg, 2 inches Hg, 3 inches Hg, or 5 inches Hg vacuum is applied to draw facial or neck tissue into the applicator 102. Other vacuum levels can be selected based on the characteristics of the tissue and desired level of comfort.

The power supply 110 can provide a direct current voltage for powering electrical elements (e.g., thermal devices) of the applicator 102 via the line 112 (FIG. 2). An operator can use an input/output device in the form of a screen 118 ("input/output device 118") of the controller 114 to control operation of the treatment system 100, and the input/output device 118 can display the state of operation of the treatment system 100 and/or progress of a treatment protocol. In some embodiments, the controller 114 can exchange data with the applicator 102 via the line 116 (FIG. 2), a wireless communication link, or an optical communication link and can monitor and adjust treatment based on, without limitation, one or more treatment profiles and/or patient-specific treatment plans, such as those described, for example, in commonly assigned U.S. Pat. No. 8,275,442. Each treatment profile and treatment plan can include one or more segments, and each segment can include temperature profiles, vacuum levels, and/or specified durations (e.g., 1 minute, 5 minutes, 10 minutes, 20 minutes, 30 minutes, 1 hour, 2 hours, etc.). Additionally, if the treatment system 100 includes multiple applicators, a treatment profile can include specific profiles for each applicator to concurrently or sequentially treat multiple treatment sites, including, but not limited to, sites along the subject's face and/or neck (e.g., submental sites, submandibular sites, etc.), abdomen, thighs, buttocks, knees, back, arms, ankle region, or other treatment sites. In some embodiments, the controller 114 can be incorporated into the applicator 102 or another component of the treatment system 100.

Figure 3:
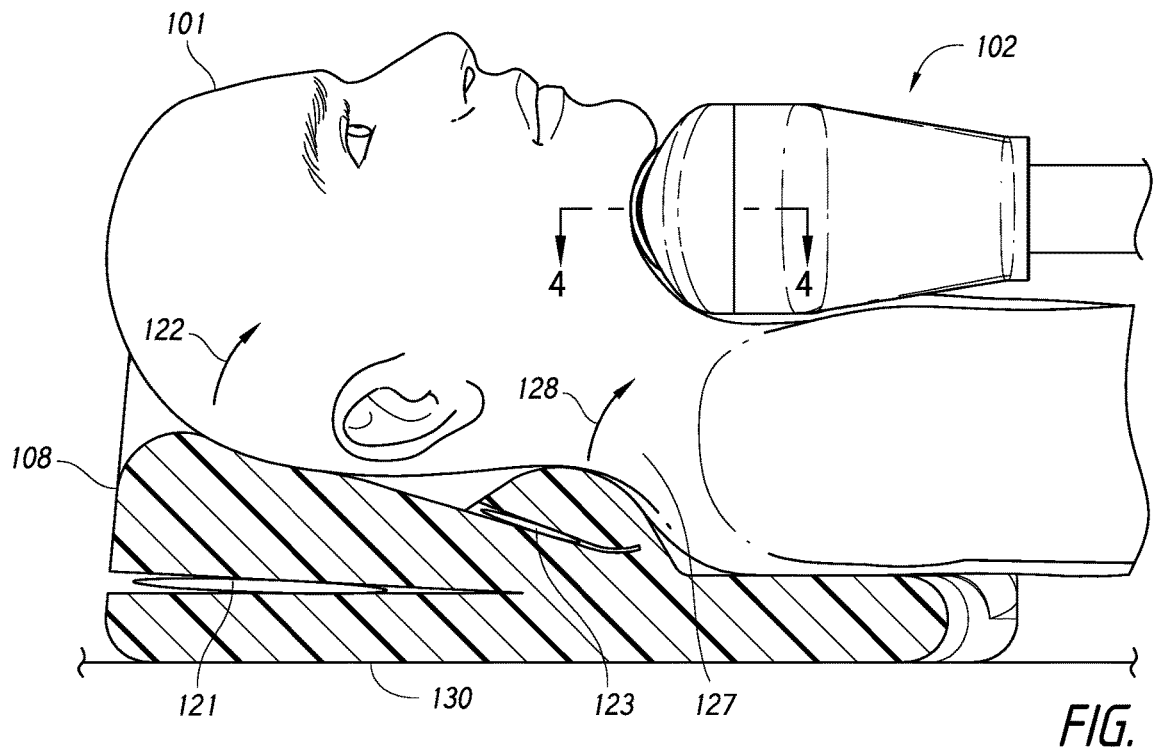
FIG. 3 is a side view of an applicator applied to a subject while the subject's head is supported by an adjustable pillow in accordance with embodiments of the technology.

FIG. 3 is a side view of the applicator 102 applied to the subject 101 while the pillow 130 (shown in cross section) supports the subject in accordance with embodiments of the technology. The pillow 130 can position the subject's body such that the submental region is at a suitable position for treatment by the applicator 102. An expandable member 121 of the head adjuster device 113 (FIG. 1) can be expanded to tilt (indicated by arrow 122) the subject's head 109. An expandable member 123 of the neck adjuster device 115 (FIG. 1) can be expanded such that the pillow 130 pushes against and moves the subject's neck 127 (indicated by arrow 128). The expandable members 121, 123 can be independently inflated/deflated any number of times in a treatment session.

D. Applicators

Figure 4:
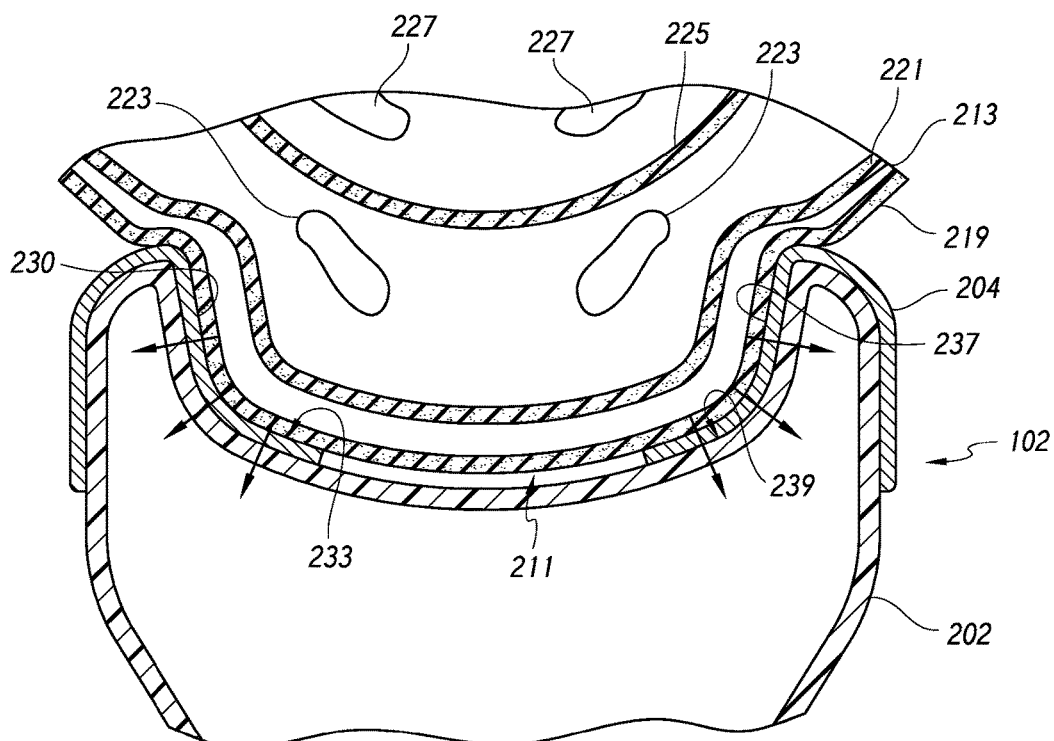
FIG. 4 is a cross-sectional view of the applicator and the subject's tissue taken along line 4-4 of FIG. 3.

FIG. 4 is a cross-sectional view of the applicator 102 taken along line 4-4 of FIG. 3. The applicator 102 can include an applicator unit 202 and a liner assembly 204. Tissue can be drawn into a tissue-receiving cavity 230 ("cavity 230") and against a patient-contact surface 237 of the liner assembly 204. The applicator unit 202 can extract heat from tissue 211 located in the tissue-receiving cavity 230. Heat (represented by arrows) from the tissue 211 can be conductively transferred through the liner assembly 204 to temperature-controlled heat-exchanging surfaces 239 of the applicator unit 202 such that heat flows across substantially all of the applicator/skin interface.

To effectively cool relatively shallow targeted submental tissue without adversely effecting deeper non-targeted tissue, the tissue 211 can be drawn against the bottom 233 of the relatively shallow tissue-receiving cavity 230. Subcutaneous lipid-rich cells in a subcutaneous layer 213 can be cooled an amount sufficient to be biologically effective in affecting (e.g., damaging and/or reducing) such lipid-rich cells without affecting non-target cells to the same or greater extent. In some procedures, platysma muscle 221, digastric muscle 223, mylohyoid muscle 225, geniohyoid muscle 227, and/or other non-targeted tissues can be generally unaffected by the treatment. In some procedures, adipose tissue in the subcutaneous layer 213 can be selectively cooled/heated without significantly affecting non-targeted tissue. Although the illustrated applicator 102 is positioned to treat mostly submental tissue, it can also be positioned to treat tissue at the submandibular region, neck region, or other target regions. Straps, harnesses, or other retaining apparatuses can secure the applicator 102 to the subject throughout therapy.

Figure 5:
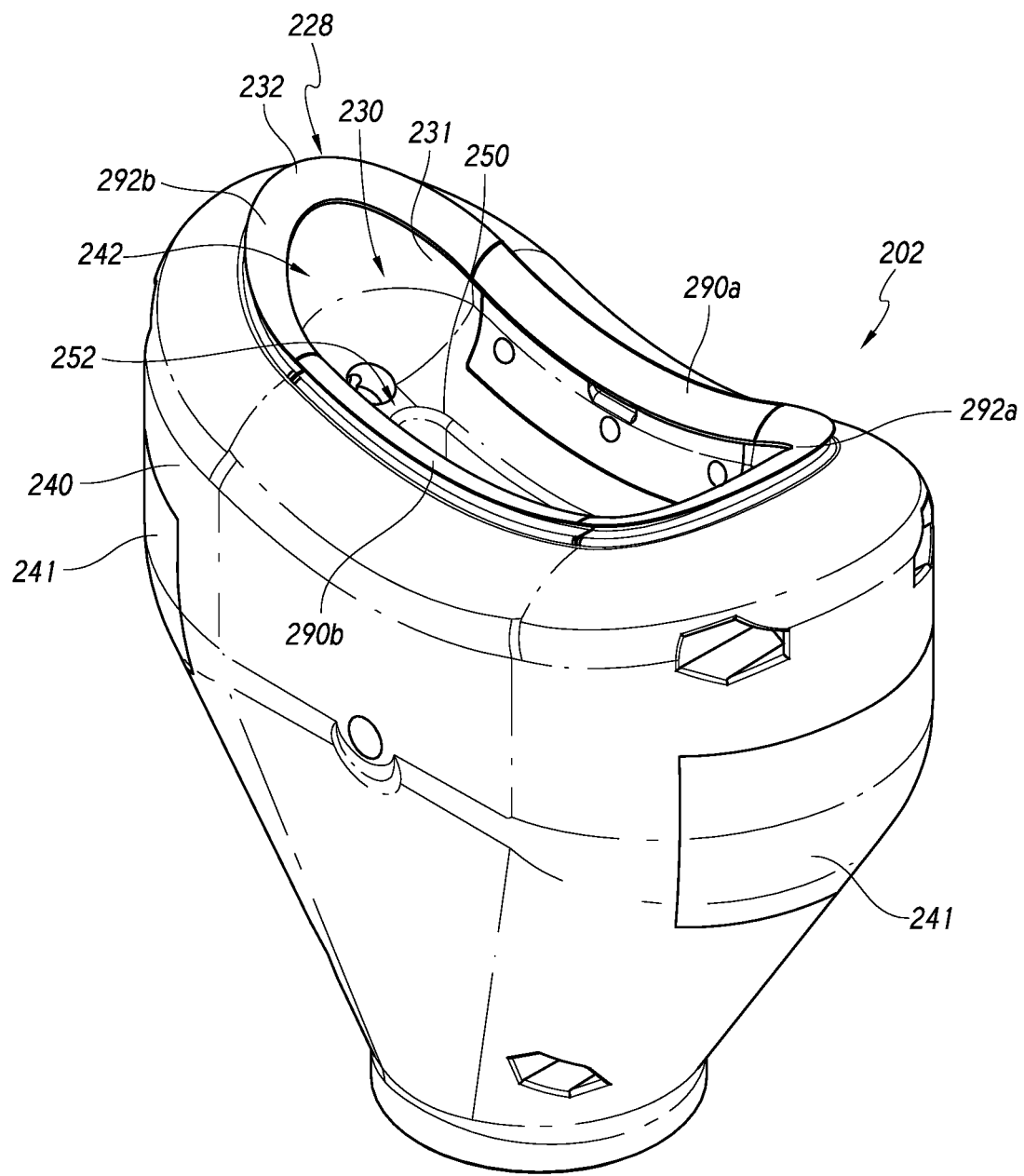
FIG. 5 is an isometric view of an applicator unit suitable for use with the system of FIG. 1 in accordance with embodiments of the technology.

FIG. 5 is an isometric view of the applicator unit 202 in accordance with embodiments of the technology. The applicator unit 202 can include a cup assembly 228 for cooling/heating tissue and a housing 240 for protecting the cup assembly 228. The cup assembly 228 can include a cup 231 and a contoured lip 232. The cup 231 can be contoured to accommodate tissue pulled into the cavity 230 and can serve as a heat sink to provide effective cooling/heating of tissue. The contoured lip 232 can define a mouth 242 of the cavity 230 and can sealingly engage, for example, a liner assembly (e.g., liner assembly 204 of FIG. 3), the subject's skin (e.g., if the contoured lip 232 is placed directly against skin), a cryoprotectant gel pad, or other surface. The contoured lip 232 can include two spaced apart arcuate lip portions 290a, 290b and side lip portions 292a, 292b connecting the lip portions 290a, 290b. Fasteners 241 (e.g., hook or loop fastener) can be coupled to or part of the housing 240. Various features of the applicator unit 202 are discussed in detail in connection with FIGS. 6-9.

Figure 6:
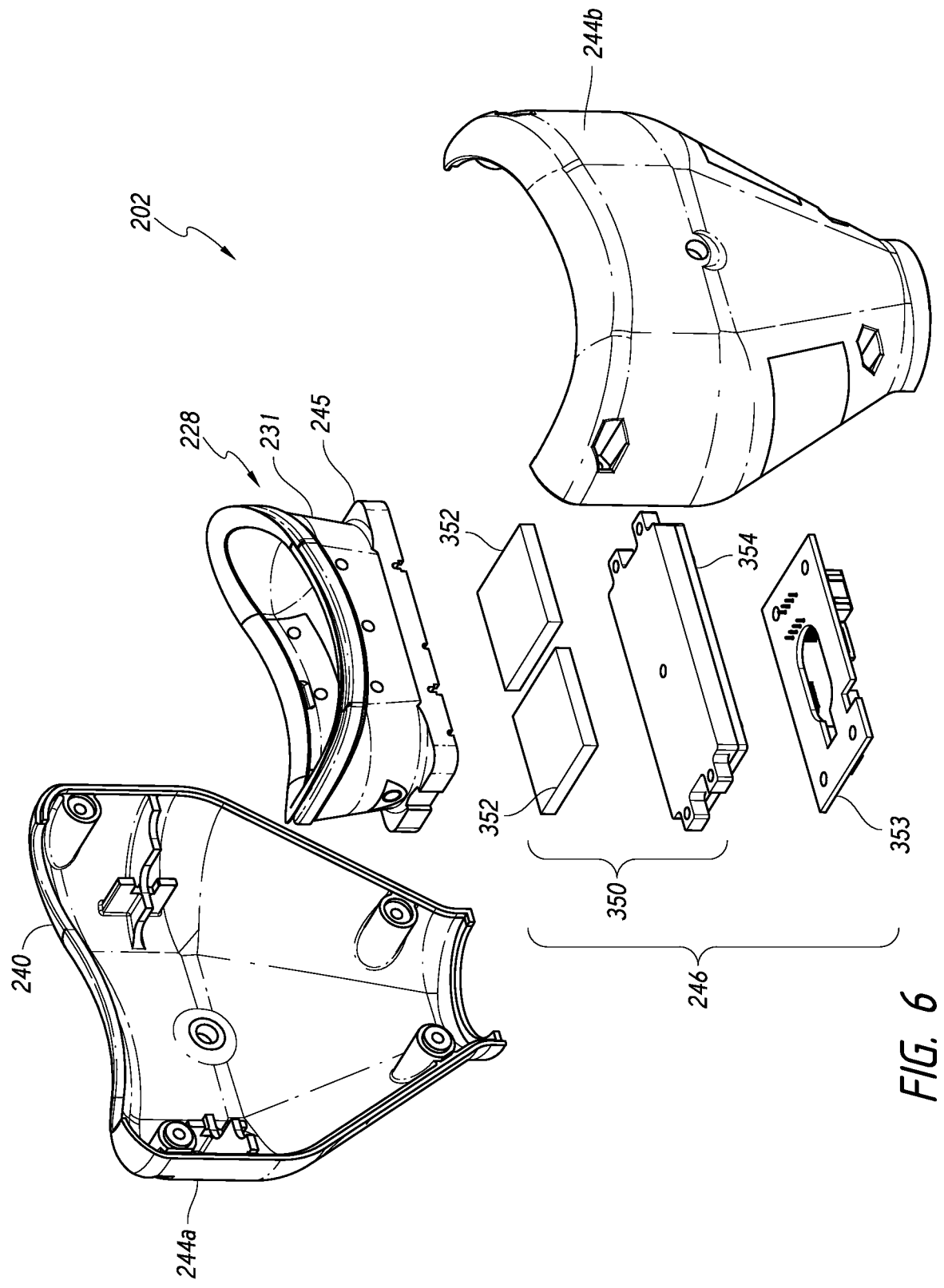
FIG. 6 is an exploded isometric view of the applicator unit of FIG. 5.

FIG. 6 is an exploded isometric view of the applicator unit 202 in accordance with embodiments of the technology. In some embodiments, including the illustrated embodiment, the housing 240 includes two housing sections 244a, 244b that cooperate to surround internal components, but the housing 240 can have a wide range of multi-piece or one-piece constructions selected based on the configuration of cooling unit 246 and/or the cup assembly 228. The cooling unit 246 can be in thermal communication with a base 245 of the cup assembly 228. In a cooling mode, the cooling unit 246 cools the cup assembly 228, and in a heating mode, the cooling unit 246 heats the cup assembly 228.

Figure 7:
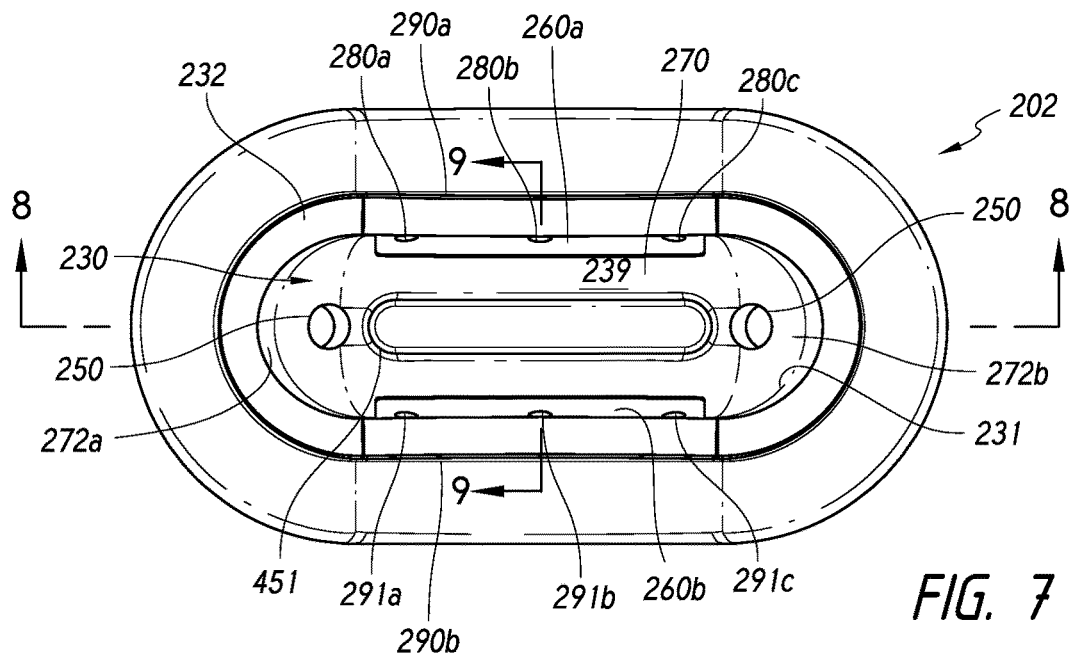
FIG. 7 is a top view of the applicator unit of FIG. 5 in accordance with embodiments of the technology.

FIG. 7 is a top view of the applicator unit 202 in accordance with embodiments of the technology. The cup 231 can include spaced apart sidewalls 260a, 260b, a bottom 270, and end portions 272a, 272b. The sidewalls 260a, 260b can be curved, flat, or combinations thereof and can extend between the end portions 272a, 272b. The bottom 270 can extend between the sidewalls 260a, 260b and can extend between the end portions 272a, 272b.

The cup 231 can be a thermally conductive cup made, in whole or in part, of a thermally conductive material for rapid cooling and/or heating to, for example, reduce treatment times and/or produce generally flat temperature profiles over the heat-exchanging surface 239 or a portion thereof. Because the subject's body heat can be rapidly conducted to the cup 231, the cooled skin can be kept at a generally flat temperature profile (e.g., ±3° C. of a target temperature) even though regions of the skin, or underlying tissue, may experience different amounts of blood flow. The thermally conductive materials can include, without limitation, metal/metal alloys (e.g., stainless steel, copper alloys, etc.), pure metal (e.g., pure copper), or other rigid or flexible high heat transfer materials such as thermally conductive plastics. In some embodiments, the thermally conductive material at room temperature can have a thermal conductivity equal to or greater than about 13 W/(mK), 50 W/(mK), 100 W/(mK), 200 W/(mK), 300 W/(mK), 350 W/(mK), and ranges encompassing such thermal conductivities. In some embodiments, the cup 231 can have a multi-piece construction with different pieces made of different materials to provide different amounts of heat flow at different locations. In other embodiments, the cup 231 has a unitary construction and is made of a single material, such as metal. The surface 239 can be a smooth surface that extends continuously along at least most of the cavity 230. When tissue is drawn against the surface 239, the skin can be slightly stretched to reduce the thickness of the skin to increase heat transfer between target tissue and the surface 239. Thus, the mechanical properties, thermal properties, shape, and/or dimensions of the cup 231 can be selected based on, for example, target treatment temperatures and/or desired volume of tissue to be drawn into the cavity 230.

One or more vacuum ports 250 can be in fluid communication with the cavity 230. The number and locations of the vacuum ports 250 can be selected based on, for example, desired tissue draw, considerations of patient comfort, and the desired vacuum level. If the vacuum level is too low, tissue will not be drawn adequately (or at all) into the cavity 230. If the vacuum level is too high, undesirable discomfort to the patient and/or tissue damage could occur. The vacuum ports 250 can be positioned near the bottom of the cavity 230 to comfortably draw the tissue deep into the cavity 230.

Vacuum ports 280a, 280b, 280c (collectively, "vacuum ports 280") can be positioned along the sidewall 260a, and vacuum ports 291a, 291b, 291c (collectively, "vacuum ports 291") can be positioned along the sidewall 260b. The vacuum ports 280, 291 can be used to draw a liner assembly, cryoprotectant gel pad, and/or tissue against the respective sidewalls 260a, 260b. In other embodiments, adhesive (e.g., pressure-sensitive adhesive), snaps, or hook and loop type fasteners can be positioned at various locations along the surface 239 and can couple a liner assembly to the applicator unit 202. In yet other embodiments, a cinching device (not shown) can couple liner assemblies to the applicator unit 202.

Figure 8:
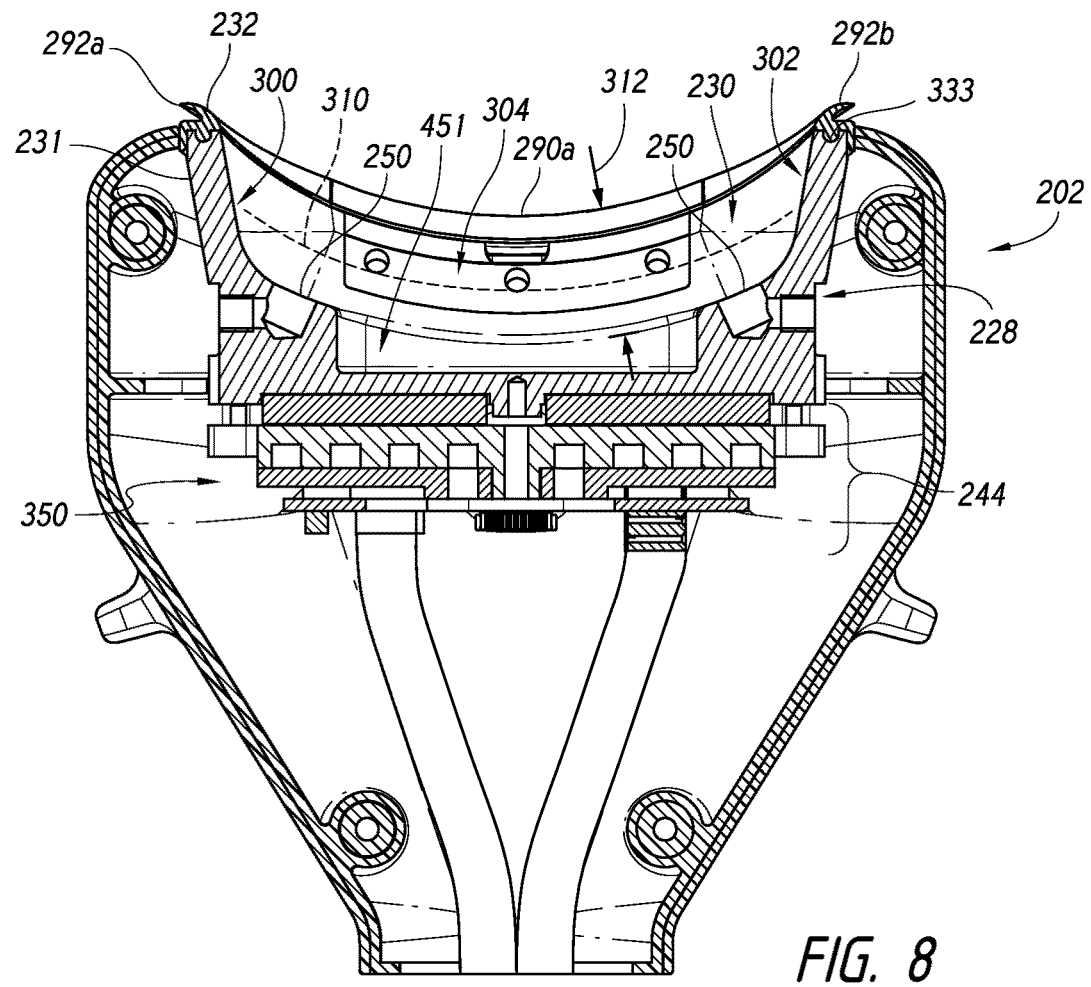
FIG. 8 is a cross-sectional view of the applicator unit taken along line 8-8 of FIG. 7.
Figure 9A:
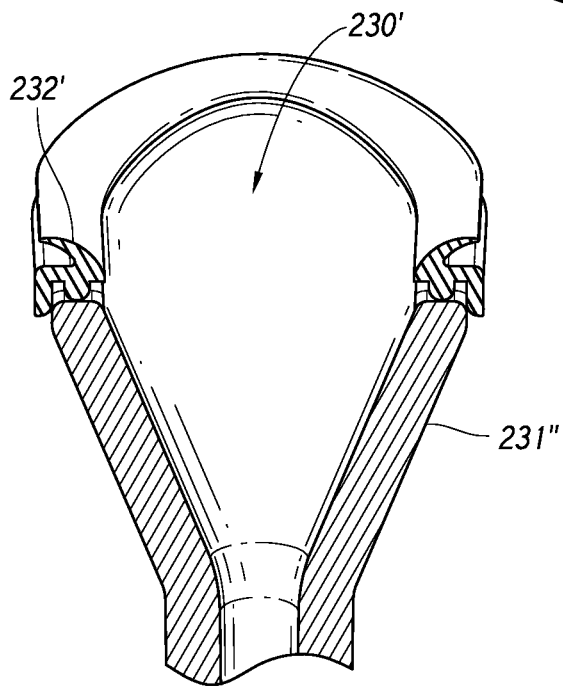
FIGS. 9A and 9B are cross-sectional views of vacuum cups in accordance with embodiments of the technology.
Figure 9:
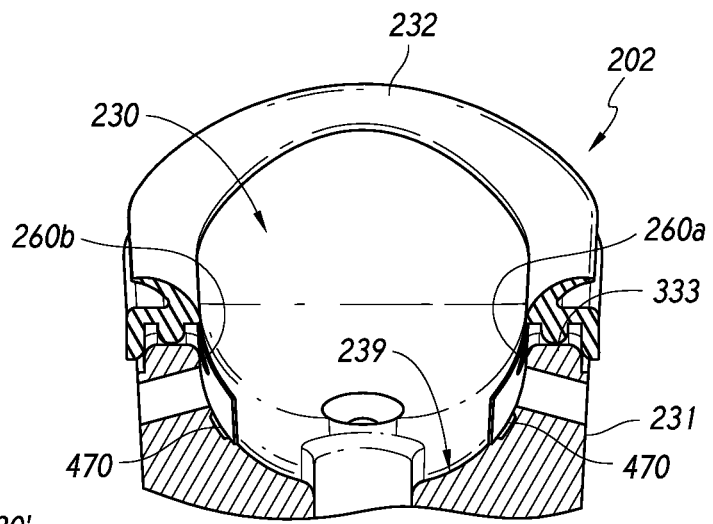
FIG. 9 is a cross-sectional view of the applicator unit taken along line 9-9 of FIG. 7.

FIG. 8 is a cross-sectional view of the applicator unit 202 taken along line 8-8 of FIG. 7. FIG. 9 is a cross-sectional view of the applicator unit 202 taken along line 9-9 of FIG. 7. Referring now to FIG. 8, cavity 230 can include a first end 300, a second end 302, and a central section 304 extending between the first and second ends 300, 302. The central section 304 can have a curved longitudinal axis 310 extending along a substantially circular path, an elliptical path, or other desired nonlinear or linear path. In some embodiments, the longitudinal axis 310 has a curvature generally equal to the curvature of at least one of the arcuate lip portions 290a, 290b (as viewed from the side). In other embodiments, the longitudinal axis 310 can have a curvature that is different than the curvature of one or both lip portions 290a, 290b and can be selected based on the shape of the subject's body.

The cavity 230 can have substantially uniform depth along most of curved longitudinal axis 310. Embodiments of the applicator unit 202 for treating submental tissue can have a maximum depth 312 equal to or less than about 0.5 cm, 2 cm, 2.5 cm, 3 cm, or 5 cm, for example. Embodiments of the applicator unit 202 for treating facial tissue can have a maximum depth 312 equal to or less than about 0.5 cm, 2 cm, or 3 cm, for example. The maximum depth 312 can be selected based on, for example, the volume of targeted tissue, characteristics of the targeted tissue, and/or desired level of patient comfort.

Figure 9B:
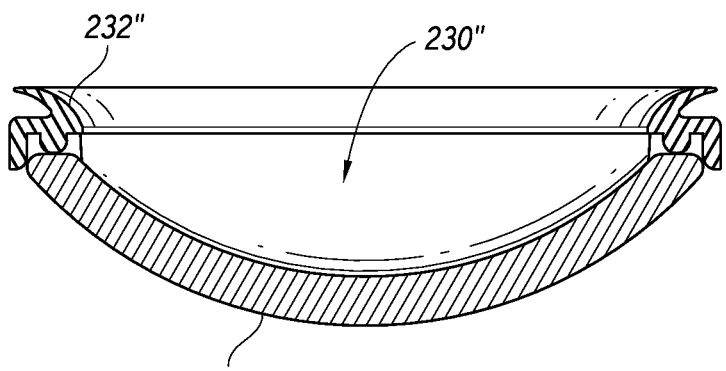

FIG. 9 shows the sidewalls 260a, 260b splayed out to facilitate conformably drawing tissue into the tissue-receiving cavity 230. The positive draft angle of the sidewalls 260a, 260b can be increased or decreased to decrease or increase, respectively, the vacuum level needed to fill the cavity 230 with tissue. Referring to FIGS. 8 and 9 together, the bottom of the cavity 230 can define a curved longitudinal profile shape in a longitudinal direction (e.g., a direction parallel to the axis 310 in FIG. 8), and the bottom of the cavity 230 can define a curved transverse profile shape in a transverse direction. In one embodiment, a radius of curvature of the longitudinal curve profile shape of FIG. 8 can be greater than a radius of curvature of the transverse curved profile of FIG. 9. The tissue-receiving cavities disclosed herein can have substantially U-shaped cross sections (see cavity 230 of FIG. 9), V-shaped cross sections (see tissue-receiving cavity 230' of FIG. 9A), or partially circular/elliptical cross-sections (see tissue-receiving cavity 230'' of FIG. 9B), as well as or other cross sections suitable for receiving tissue.

FIG. 9 shows the contoured lip 232 connected to an upper edge 333 of the cup 231. The contoured lip 232 can be made, in whole or in part, of silicon, rubber, soft plastic, or other suitable highly compliant materials. The mechanical properties, thermal properties, shape, and/or dimensions of the contoured lip 232 can be selected based on, for example, whether the contoured lip 232 contacts a liner assembly, a surface of a cryoprotectant gel pad, or the subject's skin.

Sensors 470 can be coupled to the surface 239, embedded in the cup 231, or located at other suitable positions (e.g., carried by a film applied to the cup 231). The sensors 470 can be temperature sensors, such as thermistors, positioned to detect temperature changes associated with warm tissue being drawn into the cup 231. A control module (e.g., control module 106 of FIG. 1) can interpret the detected temperature increase associated with skin contact and can monitor, for example, the depth of tissue draw and tissue contact based on the locations and amount of temperature increase. In some embodiments, the sensors 470 measure heat flux and/or pressure (e.g., contact pressure) with the skin of the patient. In yet further embodiments, the sensors 470 can be tissue impedance sensors or other sensors capable of detecting the presence and/or characteristics of tissue. Feedback from the sensors 470 can be collected in real-time and used in concert with treatment administration to efficaciously target specific tissue. The sensor measurements can also indicate other changes or anomalies that can occur during treatment administration. For example, an increase in temperature detected by the sensors 470 can indicate either a freezing event at the skin or movement of the applicator 102.

An operator can inspect the subject's skin and/or applicator 102 in response to a detected increase in temperature. Methods and systems for collection of feedback data and monitoring of temperature measurements are described in commonly assigned U.S. Pat. No. 8,285,390.

Referring again to FIG. 6, the cooling unit 246 can be mounted directly to the cup assembly 228 and can include a thermal device 350 and a connection assembly 353. The thermal device 350 can include, without limitation, one or more thermoelectric elements (e.g., Peltier-type elements), fluid-cooled elements, heat-exchanging units, or combinations thereof. In some embodiments, the thermal device 350 includes thermoelectric elements 352 for cooling/heating the base 245 and a fluid-cooled element 354 for cooling/heating the thermoelectric elements 352. In a cooling mode, the fluid-cooled element 354 can cool the backside of the thermoelectric elements 352 to keep the thermoelectric elements 352 at or below a target temperature. In a heating mode, the fluid-cooled element 354 can heat the backside of the thermoelectric elements 352 to keep the thermoelectric elements 352 at or above a target temperature. Although the illustrated thermal device 350 has two thermoelectric elements 352, it can have any desired number of thermoelectric elements 352 at various locations about the cup 231. In other embodiments, the thermal device 350 has only fluid-cooled elements or only non-fluid cooled thermoelectric elements. The configurations and components of the thermal device 350 can be selected based on the desired power consumption and targeted temperatures. The connection assembly 353 can include circuitry, a circuit board, fittings (e.g., inlet ports, outlet ports, etc.), or the like. The cooling unit 246 can also be incorporated into part of the cup assembly 228. In such embodiments, the thermoelectric elements 352 can be embedded or otherwise disposed in the cup 231 to reduce the distance from the tissue to the thermoelectric elements 352.

Figure 10:
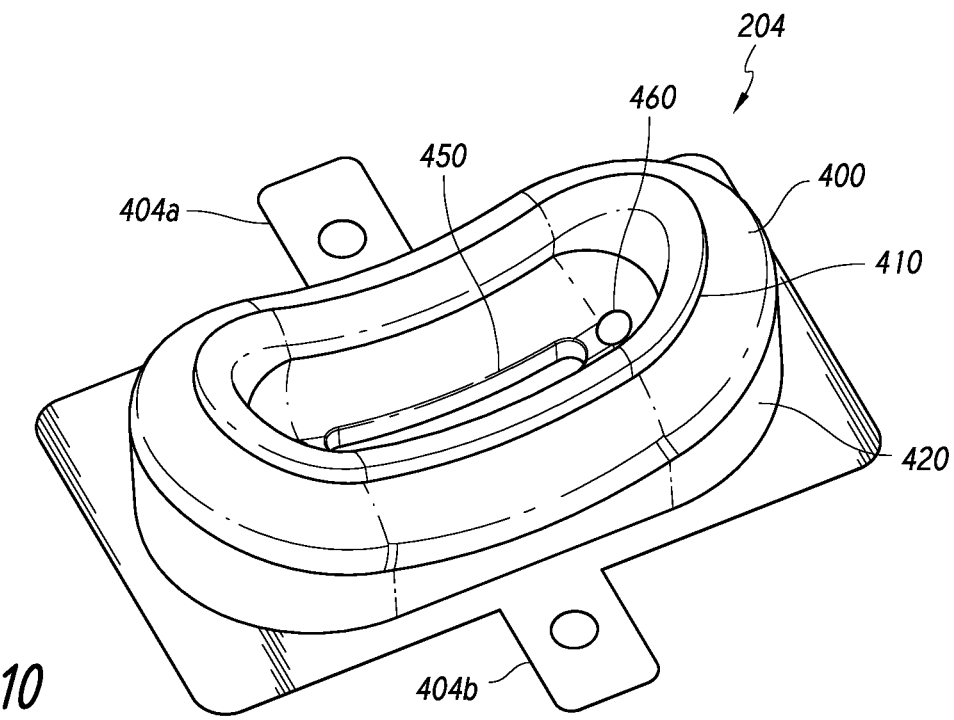
FIG. 10 is an isometric view of a liner assembly in accordance with embodiments of the technology.
Figure 11:
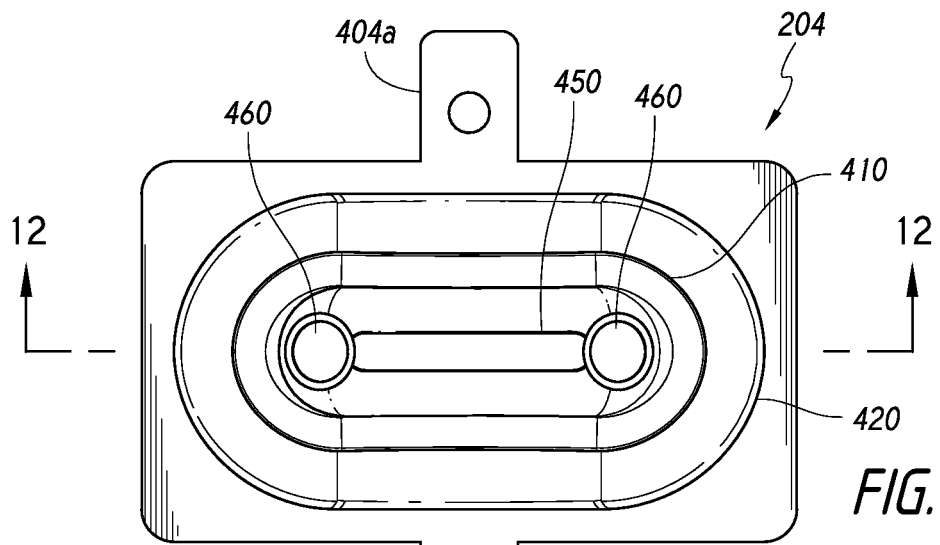
FIG. 11 is a top view of the liner assembly of FIG. 10.
Figure 12:
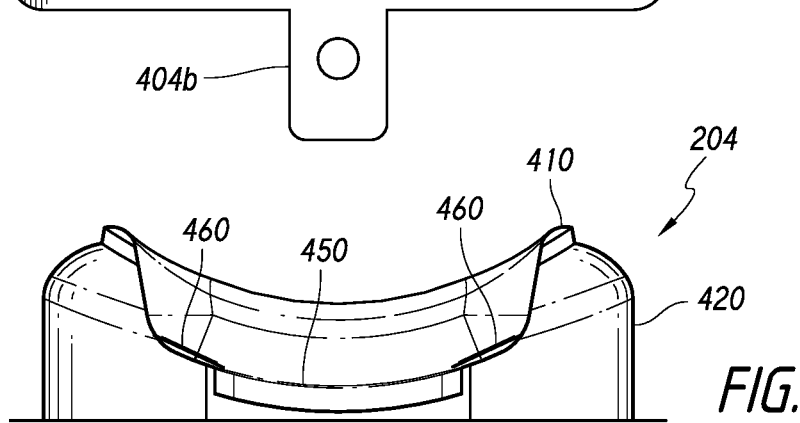
FIG. 12 is a cross-sectional view of the liner assembly taken along line 12-12 of FIG. 11.

FIG. 10 is an isometric view of the liner assembly 204 in accordance with one embodiment. FIG. 11 is a top view of the liner assembly 204 of FIG. 10. FIG. 12 is a cross-sectional view of the liner assembly 204 taken along line 12-12 of FIG. 11. When the liner assembly 204 is positioned on an applicator unit, the liner assembly 204 can provide a sanitary surface for contacting a patient and can also effectively transfer heat between the subject and the applicator unit. After treatment, the liner assembly 204 can be discarded or sanitized and reused.

The liner assembly 204 can include a cup liner 400 for overlaying the heat transfer surface of an applicator unit and attachment members 404a, 404b for securing the liner assembly 204 to the applicator unit. The cup liner 400 can include a lip portion 410 and a main body 420. When the applicator unit is inserted into the main body 420, the lip portion 410 can surround the mouth of a tissue receiving cavity and an elongated opening 450 can be aligned with a trench (see trench 451 of FIG. 8) of the applicator unit, and openings 460 can be aligned with the vacuum ports of the applicator unit. In highly compliant embodiments, the liner assembly 204 can be made, in whole or in part, of rubber, soft plastic, or other compliant material.

Liner assemblies can also be a film, a sheet, a sleeve, or other component suitable for defining an interface surface to prevent direct contact between the applicator unit and the subject's skin to reduce the likelihood of cross-contamination between patients, minimize cleaning requirements, etc. Exemplary protective liners can be sheets, sleeves, or other components constructed from latex, rubber, nylon, Kevlar®, or other substantially impermeable or semi-permeable material. Further details regarding a patient protection device may be found in U.S. Patent Publication No. 2008/0077201. A liner or protective sleeve may be positioned between the absorbent and the applicator to shield the applicator and to provide a sanitary barrier that is, in some embodiments, inexpensive and thus disposable.

E. Treatment Methods

Figure 15:
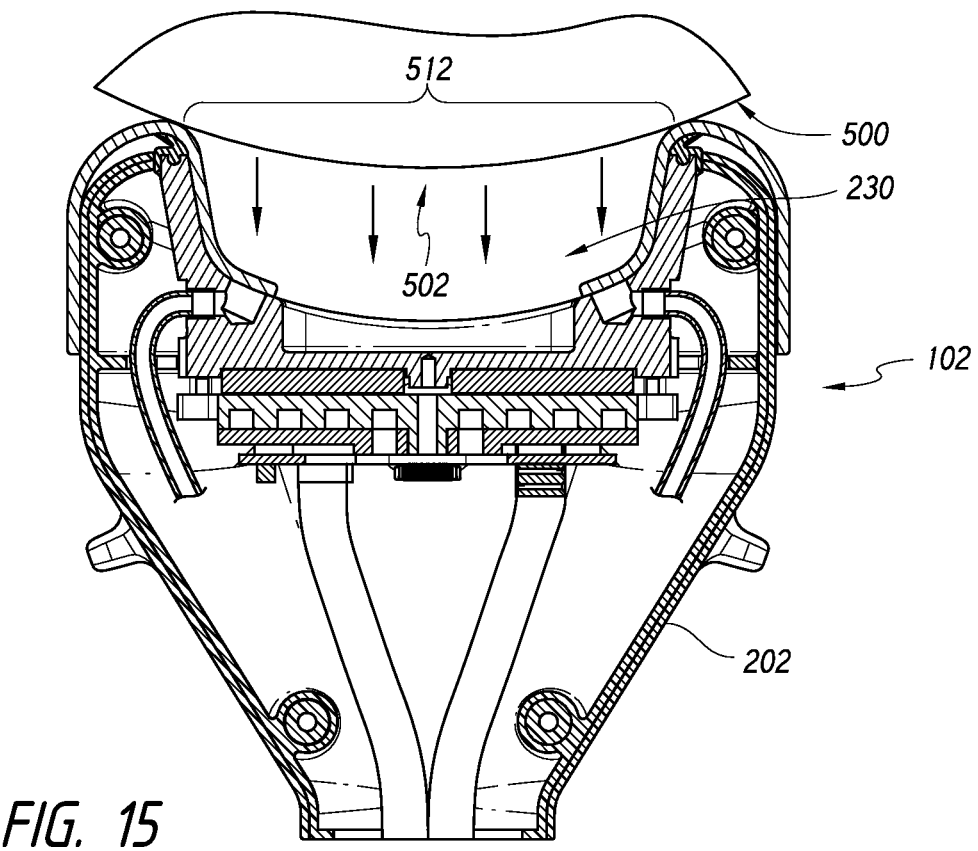
FIG. 15 is a cross-sectional view of the applicator before tissue has been drawn into a tissue-receiving cavity of the applicator.
Figure 16:
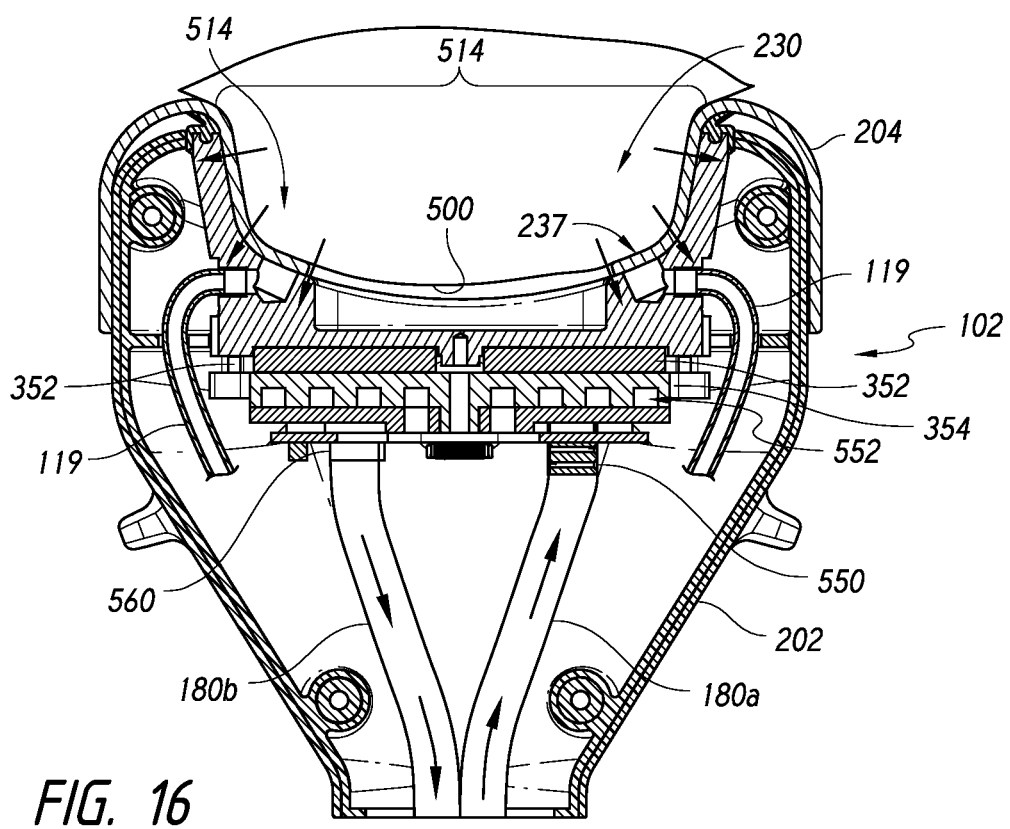
FIG. 16 is a cross-sectional view of the applicator after tissue has been drawn into the tissue-receiving cavity.
Figure 17:
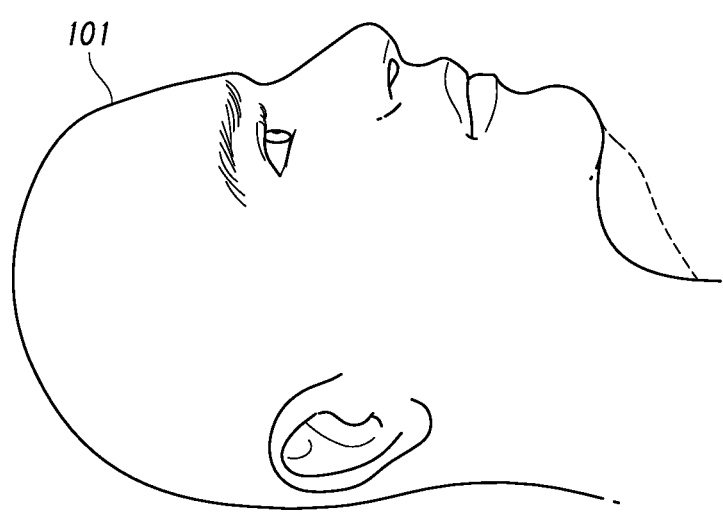
FIG. 17 shows the subject after cryotherapy has been performed.

FIGS. 13-17 are a series of views of a method of performing cryotherapy in accordance with various embodiments of the present technology. Generally, targeted tissue can be drawn into the applicator 102 until the tissue is in thermal contact a region of the cup assembly 228 located at a bottom of the cavity 230. The cup assembly 228 can be cooled to extract heat from the tissue so as to cool/heat targeted tissue an amount sufficient to be biologically effective in damaging and/or reducing targeted cells. FIG. 17 shows a pretreatment tissue profile of a double chin in phantom line and the post treatment tissue profile in solid line. Various details of operation are discussed in detail below.

Figure 13:
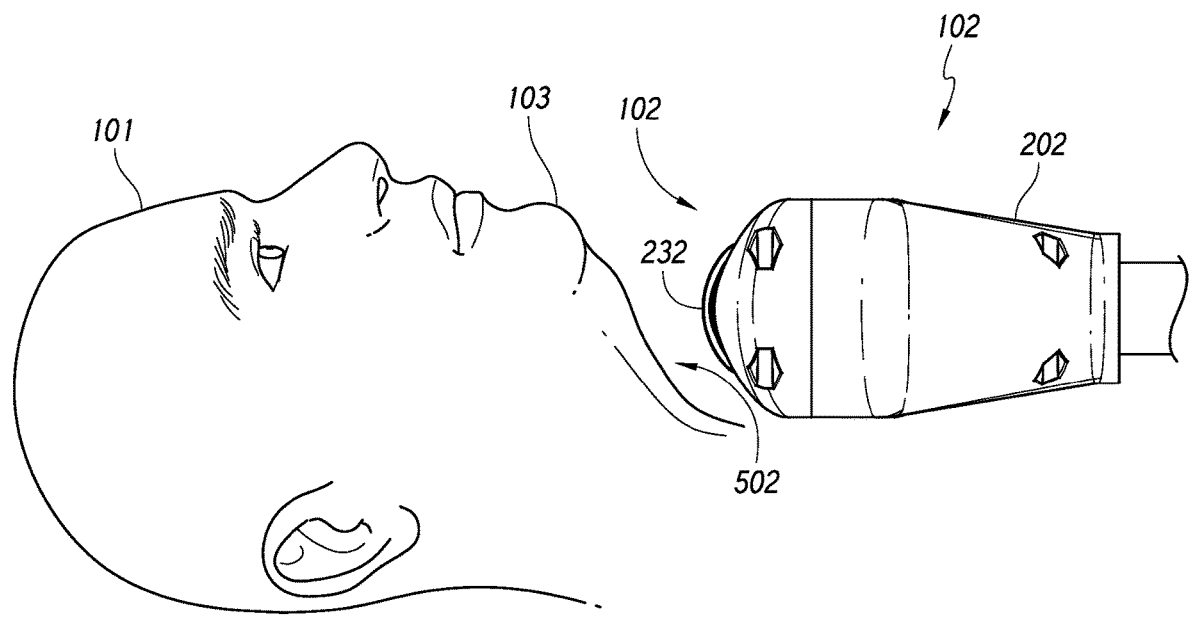
FIG. 13 shows an applicator ready to be placed against a subject's skin in accordance with embodiments of the technology.

FIG. 13 shows the applicator 102 ready to be placed at a treatment site 502. In procedures for reducing a double chin, the applicator 102 can be aligned with and placed generally at the submental region (i.e., the submental triangle). Although the subject's head is shown at a generally horizontal orientation, the subject's head can be held at other orientations. For example, a pillow (e.g., pillow 130 of FIG. 1) or other support device can be used to elevate, tilt, or otherwise position the subject's head, neck, shoulders, and/or other body parts. The applicator 102 can be placed against the subject such that it extends laterally across the submental triangle or a portion thereof. It will be appreciated that the applicator 102 can be placed at other locations along the patient's body and the orientation of the applicator 102 can be selected to facilitate a relatively close fit.

Figure 14:
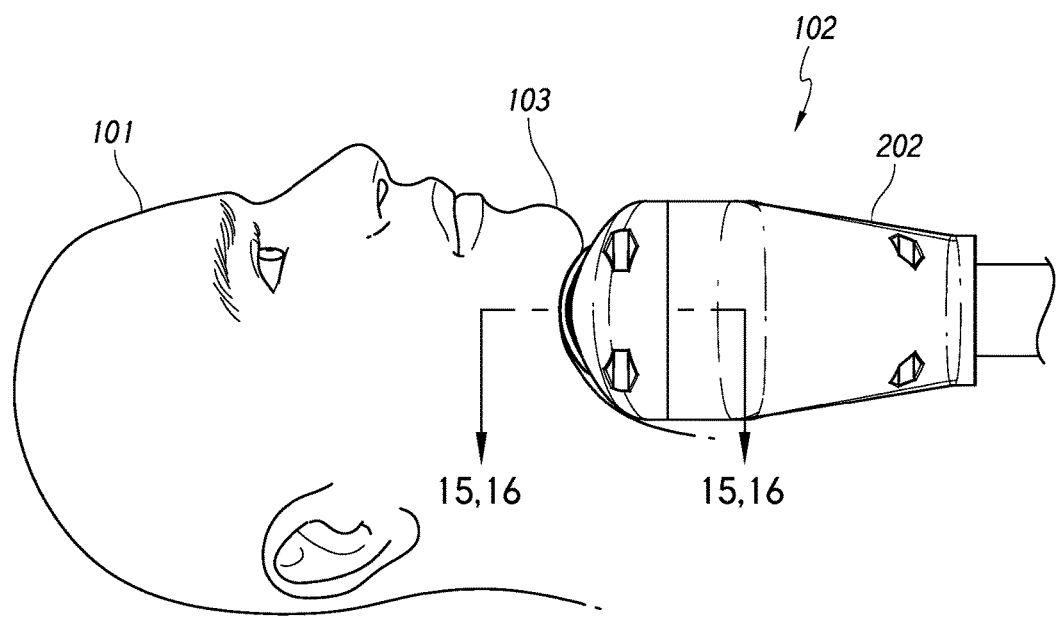
FIG. 14 shows the applicator contacting the subject's skin.

FIG. 14 shows the applicator 102 placed against the subject's skin. FIG. 15 is a cross-sectional view of the applicator 102 contacting the subject's skin 500 before drawing tissue. FIG. 16 is a cross-sectional view of the applicator 102 after tissue has been drawn into the cavity 230. Although not shown in FIGS. 13-16 for ease of illustration, other elements, materials, components (e.g., gel pads, absorbents, etc.) can be located between the skin 500 and the applicator 102. U.S. Pub. No. 2007/0255362 and U.S. Patent Publication No. 2008/0077201 and U.S. application Ser. No. 14/610,807 disclose components, materials (e.g., coupling gels, cryoprotectants, compositions, etc.), and elements (e.g., coupling devices, liners/protective sleeves, absorbents, etc.) that can be placed between the skin 500 and the applicator 102.

Referring to FIGS. 15 and 16, when a vacuum is applied, the skin 500 can be moved (indicated by arrows in FIG. 15) towards the bottom of the cavity 230. The vacuum level can be selected to comfortably pull the tissue into contact with the desired area of the applicator 102, and the skin 500 and underlying tissue can be pulled away from the subject's body which can assist in cooling underlying tissue by, e.g., lengthening the distance between targeted subcutaneous fat and the muscle tissue. After a sufficient amount of tissue fills most or all of the cavity 230, the tissue is cooled/heated. FIG. 16 shows mostly submental tissue located in the cavity 230. For example, substantially all the tissue 514 can be submental tissue to alter only the submental region. In other procedures, tissue at the submandibular region can be drawn into the cavity 230 to reduce, for example, jowl fat.

Because a target volume of fat may be relatively small and localized, the applicator 102 can provide well-defined margins of the treatment area. In some embodiments, the applicator 102 can conductively cool an area equal to or less than about 20 cm$^2$, 30 cm$^2$, or 40 cm$^2$ to avoid damaging non-targeted tissue (e.g., tissue adjacent to the submental region). In some embodiments, the patient-contact surface 237 can have a surface area equal to or less than about 20 cm$^2$, 30 cm$^2$, or 40 cm$^2$. An operator can have an array of applicators with different dimensions so that the operator can select an applicator to match a patient's anatomy.

The control module 106 (FIG. 1) can automatically begin heating/cooling the tissue. In other embodiments, the control module 106 (FIG. 1) can notify the operator that the applicator 102 is ready for treatment. The operator can inspect the applicator 102 and can begin treatment using the control module 106. Heat (represented by arrows in FIG. 16) can be transferred from targeted tissue to the thermoelectric elements 352. Coolant can flow through an inlet port 550 connected to the fluid line 180a. The coolant can circulate through passages 552 to absorb heat from the thermoelectric elements 352 and can exit the passages 552 via the outlet port 560 connected to the fluid line 180b. The heated coolant can flow back to the control module 106 (FIG. 1) for cooling.

In contrast to invasive procedures in which coolant is injected directly into targeted tissue, each of the sidewalls 260a, 260b and bottom 270 (FIG. 7) can conductively cool tissue to produce a desired temperature in target tissue without bruising, pain, or other problems caused by injections and perfusion of injected fluid. For example, perfusion of injected fluid can affect the thermal characteristics of the treatment site and result in undesired temperature profiles. As such, the non-invasive conductive cooling provided by the applicator 102 can be more accurate than invasive procedures that rely on injecting fluids. The illustrated targeted tissue of FIG. 16 can be cooled to a temperature range from about −20° C. to about 10° C., from about 0° C. to about 20° C., from about −15° C. to about 5° C., from about −5° C. to about 15° C., or from about −10° C. to about 0° C. In one embodiment, the patient-contact surface 237 can be kept at a temperature less than about 5° C. to extract heat from subcutaneous lipid-rich cells such that those cells are selectively reduced or damaged. Because non-lipid-rich cells usually can withstand colder temperatures better than lipid-rich cells, the subcutaneous lipid-rich cells can be injured selectively while maintaining the non-lipid-rich cells (e.g., non-lipid-rich cells in the dermis and epidermis).

Lines 119 of FIG. 16 can provide sufficient vacuum to hold the skin 500 against the patient-contact surface 237. The tissue 514 can fill substantially the entire cavity 230. For example, the tissue 514 can occupy at least 70%, 80%, 90%, or 90% of the volume of the cavity 230 to avoid or minimize air pockets that may impair heat transfer. The restraint apparatus 107 of FIG. 1 can be adjusted such that the applicator 102 applies sufficient pressure to reduce, limit, or eliminate blood flow to deeper tissue to improve cooling efficiency because blood circulation is one mechanism for maintaining a constant body temperature of about 37° C. Blood flow through the dermis and subcutaneous layer of the tissue is a heat source that counteracts the cooling of the targeted tissue (e.g., sub-dermal fat). If the blood flow is not reduced, cooling the subcutaneous tissues would require not only removing the specific heat of the tissues but also that of the blood circulating through the tissues. Thus, reducing or eliminating blood flow through the tissue 514 can improve the efficiency of cooling and avoid excessive heat loss from the dermis and epidermis.

It will be appreciated that while a region of the body has been cooled or heated to the target temperature, in actuality that region of the body may be close but not equal to the target temperature, e.g., because of the body's natural heating and cooling variations. Thus, although the applicator 102 may attempt to heat or cool the target tissue to the target temperature or to provide a target heat flux, the sensors 470 (FIG. 9) may measure a sufficiently close temperature or heat flux. If the target temperature or heat flux has not been reached, operation of the cooling unit can be adjusted to change the heat flux to maintain the target temperature or "set-point" selectively to affect targeted tissue. When the prescribed segment duration expires, the next treatment profile segment can be performed.

FIG. 17 shows subject after completing cryotherapy with the pretreatment tissue profile of a double chin (shown in phantom line) and the post treatment tissue profile without the double chin (shown in solid line). It may take a few days to a few weeks, or longer, for the adipocytes to break down and be absorbed. A significant decrease in fat thickness may occur gradually over 1-3 months following treatment. Additional treatments can be performed until a desired result is achieved. For example, one or more treatments can be performed to substantially reduce (e.g., visibly reduce) or eliminate a double chin.

The treatment procedure of FIGS. 13-17 can also involve use of cryoprotectant between the applicator 102 and the skin. The cryoprotectant can be a freezing point temperature depressant that may additionally include a thickening agent, a pH buffer, a humectant, a surfactant, and/or other additives. The temperature depressant may include, for example, polypropylene glycol (PPG), polyethylene glycol (PEG), dimethyl sulfoxide (DMSO), or other suitable alcohol compounds. In a particular embodiment, a cryoprotectant may include about 30% polypropylene glycol, about 30% glycerin (a humectant), and about 40% ethanol. In another embodiment, a cryoprotectant may include about 40% propylene glycol, about 0.8% hydroxyethylcellulose (a thickening agent), and about 59.2% water. In a further embodiment, a cryoprotectant may include about 50% polypropylene glycol, about 40% glycerin, and about 10% ethanol. Other cryoprotectants or agents can also be used and can be carried by a cotton pad or other element. U.S. application Ser. No. 14/610,807 is incorporated by reference in its entirety and discloses various compositions that can be used as cryoprotectants.

F. Applicator Units

FIGS. 18-22 are isometric views of applicators in accordance with embodiments of the present technology. The description of the applicator 102 (FIGS. 1-17) applies equally to the applicators of FIGS. 18-21 unless indicated otherwise. FIG. 18 shows an applicator 600 that includes a cup 601 defining a tissue-receiving cavity 610. The cup 601 has sidewalls 602, end portions 603, and a bottom 604. A thermally conductive edge 616 (e.g., a rounded edge or a blunt edge) can be made of metal or other thermally conductive material capable of cooling/heating margins of the treatment site. An array of vacuum ports 612 (one labeled in FIG. 18) are in fluid communication with the tissue-receiving cavity 610. A base 624 can be in thermal communication with the cup 601 and can include, without limitation, one or more thermal elements, controllers, or the like.

FIG. 19 shows an applicator 630 that includes a cup 631 and a base 656. The cup 631 has sidewalls 632, end portions 633, and a bottom 634 and defines a tissue-receiving cavity 640. A lip portion 642 is coupled to the cup 631 and flares outwardly. The cavity 640 (as viewed from above) can have an elongate shape (e.g., generally elliptical shape, rounded rectangle shape, etc.), a circular shape, or other suitable shape for receiving tissue. A vacuum port 652 is in fluid communication with the tissue-receiving cavity 640.

FIG. 20 shows an applicator 660 that includes a cup 661 with sidewalls 662, end portions 663, and a bottom 664 and can define a tissue-receiving cavity 670. A lip portion 672 can be a bladder seal or other sealing member. A vacuum port 675 can provide a vacuum for drawing the submental tissue into the cup 661, and vacuum ports 677 can provide a vacuum for drawing a liner assembly or skin against the cup 661. FIG. 21 shows the applicator 660 with a base 680 that serves as a heat spreader to increase heat flows.

Exemplary components and features that can be incorporated into the applicators disclosed herein are described in, e.g., commonly assigned U.S. Pat. No. 7,854,754 and U.S. Patent Publication Nos. 2008/0077201, 2008/0077211, 2008/0287839, 2011/0238050 and 2011/0238051. The patient protection devices (e.g., liners or liner assemblies) may also include or incorporate various storage, computing, and communications devices, such as a radio frequency identification (RFID) component, allowing for example, use to be monitored and/or metered. Additionally, restraint apparatuses or components disclosed herein can be used to perform the method discussed in connection with FIGS. 13-16. For example, the restraint apparatus 107 can be used to hold the applicators disclosed herein to perform the cryotherapy of FIGS. 13-16.

Figure 22:
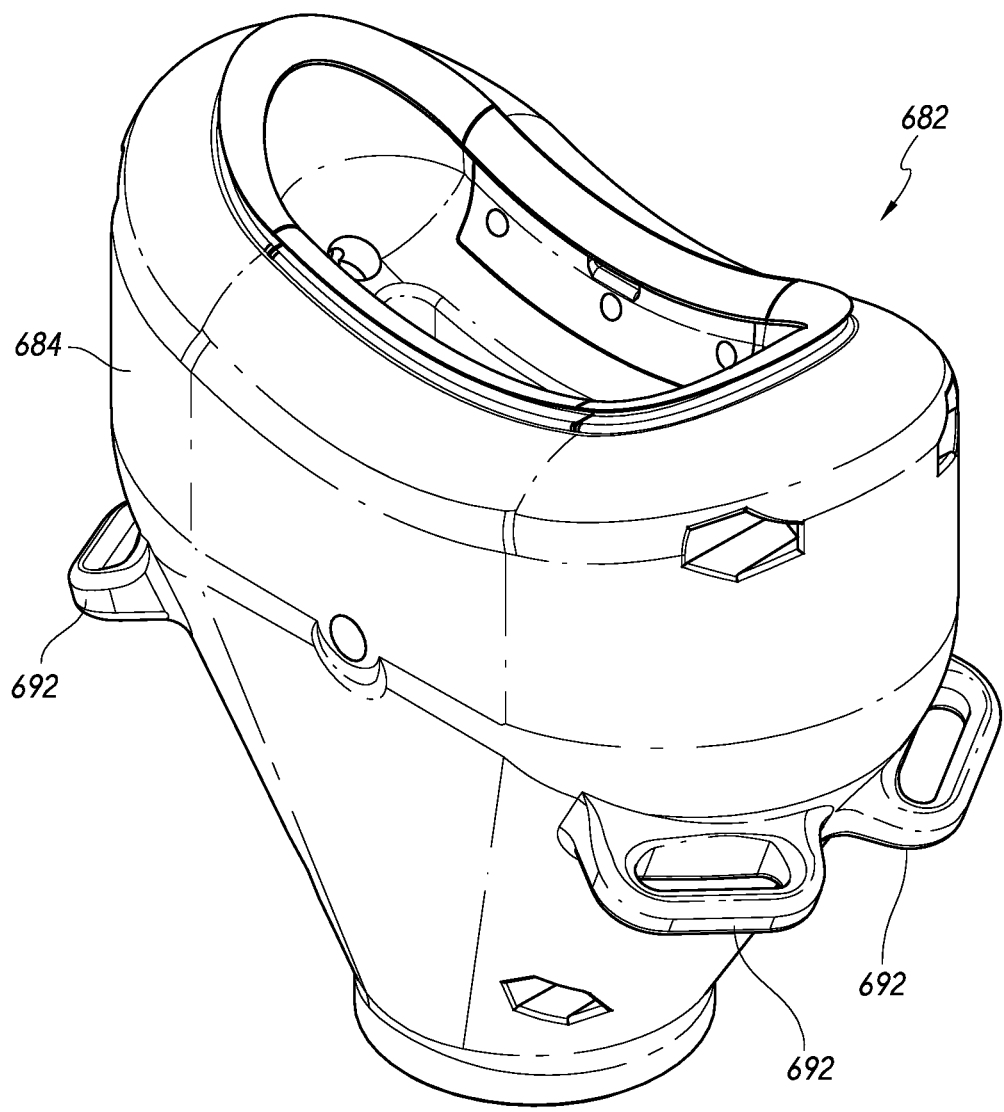
FIG. 22 is an isometric view of an applicator unit in accordance with embodiments of the technology.

FIG. 22 is an isometric view of an applicator 682 in accordance with embodiments of the technology. The applicator 682 is generally similar to the applicator 102 discussed in connection with FIGS. 1-17. The applicator 682 of FIG. 22 includes a housing 684 with coupling features in the form of loops 692 configured to receive restraints, such as flexible straps, belts, etc.

Figure 23B:
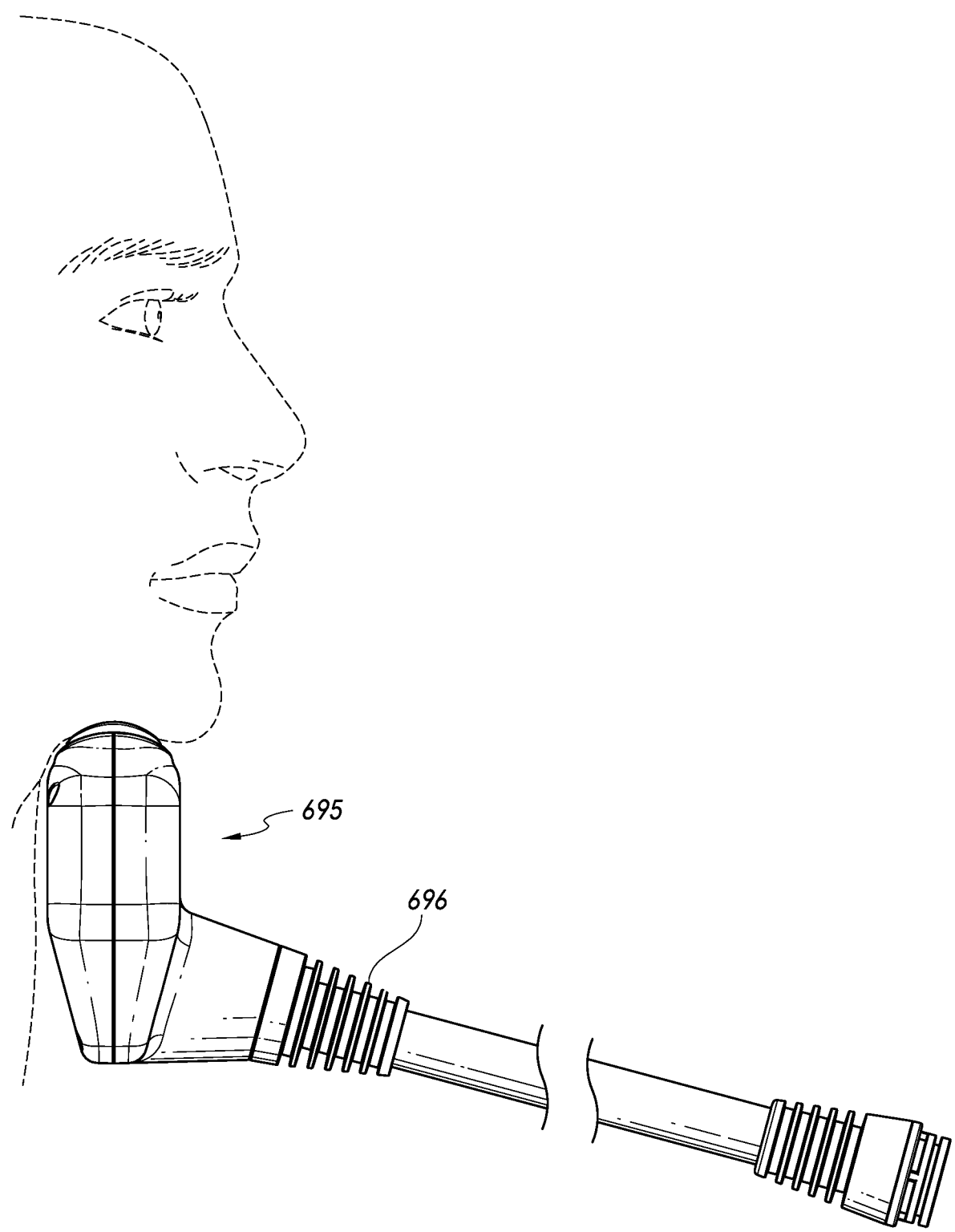
FIG. 23B is a side view of the applicator and connector of FIG. 23A.

FIG. 23A is an isometric view of an applicator 695 suitable for use with treatment systems disclosed herein. The applicator 695 can be generally similar to the applicators discussed in connection with FIGS. 1-23. The applicator 695 is connected to a connector 104 via a flexible joint 696. FIG. 23B shows the flexible joint 696 extending from a side of the applicator 695 or from any other suitable location along the applicator 695.

Figure 23D:
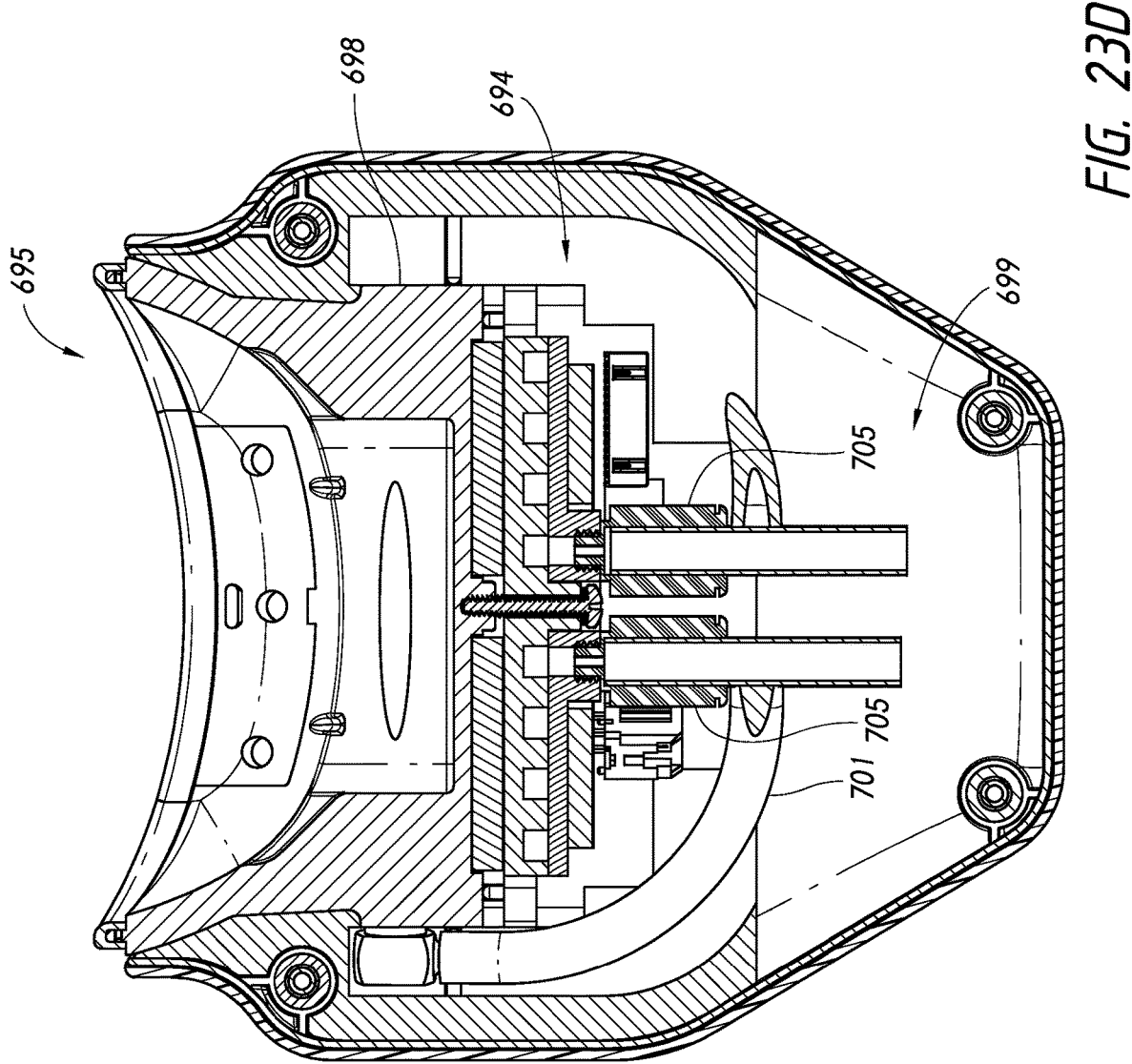
FIG. 23D is a cross-section view of the applicator of FIG. 23A.

FIG. 23C is an exploded isometric view of the applicator 695 in accordance with embodiments of the technology, and FIG. 23D is a cross-sectional view of the applicator of FIG. 23A. Referring to these figures, a housing 693 of the applicator 695 can include multiple housing sections 697 that cooperate to surround and protect internal components, such as a cooling unit 694. The cooling unit 694 can heat or cool a conductive cup 698. A manifold system 699 can include lines 701 in fluid communication with ports 703 (one identified in FIG. 23C) of the cup 698. The manifold system 699 can also include coolant lines 705 (FIG. 23D) that provide coolant to and take away coolant from the cooling unit 694. The applicator 695 can have other components, including liner assemblies, sensors, manifolds, vibrators, massage devices, or combinations thereof. Additionally, the manifold system 699 can include vacuum lines 687 that can be fluid communication with vacuum ports 688 (two identified in FIG. 23C) of the cup 698. The vacuum lines 687 can be used to draw a vacuum to hold a liner assembly against the conductive cup 698.

Although noninvasive applicators are illustrated and discussed with respect to FIGS. 1-23D, minimally invasive applicators may also be employed. As an example, a cryoprobe, an electrode, an injector (e.g., a needle), and/or other invasive component may be incorporated into the applicators disclosed herein and can be inserted directly into the targeted tissue (e.g., subcutaneous adipose tissue) to cool, freeze, or otherwise thermally process targeted tissue. Treatment systems and applicators disclosed herein can also include elements (e.g., electrodes, vibrators, etc.) for delivering energy, such as radiofrequency energy, ultrasound energy (e.g., low frequency ultrasound, high frequency ultrasound, etc.), mechanical massage, and/or electric fields. The energy can be selected to affect treatment by, for example, heating tissue. Additionally or alternatively, energy can be used to affect the crystal formation in non-targeted tissues while allowing cooling of the targeted tissue. In non-targeted cells or structures, non-thermal energy parameters may be selected to reduce ice crystal size and/or length, reduce freezing lethality, or the like. In targeted cells or structures, non-thermal energy parameters may be selected to enhance crystal nucleation. Thus, energy can be selectively applied to control therapy. The treatment systems disclosed herein may be used with a substance that may provide a thermal coupling between the subject's skin and the thermal element(s) to improve heat transfer therebetween. The substance may be a fluid, e.g., a liquid, a gel, or a paste, which may be hygroscopic, thermally conductive, and biocompatible.

G. Restraint Systems

Figure 24:
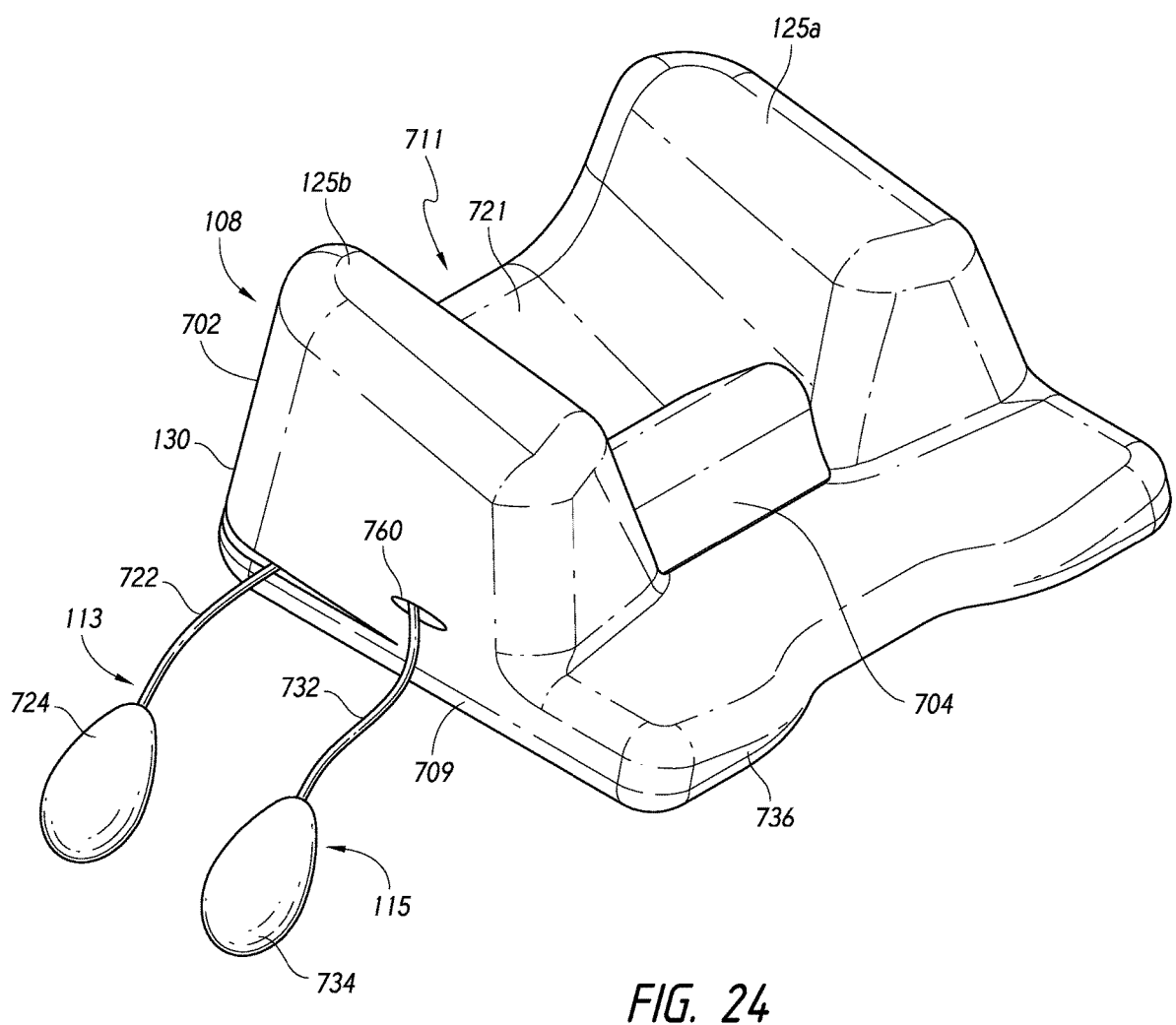
FIG. 24 is an isometric view of a head support assembly in accordance with embodiments of the present technology.

FIG. 24 is an isometric view of the head support assembly 108 in accordance with embodiments of the present technology. The pillow 130 can include a deployable head cradle portion 702, a neck support portion 704, and a shoulder support portion 736. The head cradle portion 702 can include the vertical side portions 125a, 125b and a central region 721 therebetween. The side portions 125a, 125b are positioned to contact opposite sides of a subject's head located in a concave head-receiving region 711. Movement of the head cradle portion 702 and the neck support portion 704 for positioning the patient's body is discussed in connection with FIGS. 25 and 26.

The head adjuster device 113 can include a pressurization device in the form of a pump 724 and a conduit 722. The conduit 722 fluidically couples the pump 724 to an expandable member (not shown) positioned within the pillow 130. For example, the expandable member can be positioned between the head cradle portion 702 and the base 709. The pump 724 can be manually pumped to move the head cradle portion 702 to achieve desired tilt of the subject's head. The neck adjuster device 115 includes a pressurization device in the form of a pump 734 and a conduit 732. The conduit 732 can extend through the side portion 125b and to an expandable member located generally underneath the neck support portion 704. The pump 734 can be manually pumped to move the neck support portion 704 to achieve desired neck tilt of the subject. In various embodiments, the adjuster devices disclosed herein can include, without limitation, one or more motorized pumps, valves, pressure regulators, pneumatic drive devices, mechanical drive devices, or other suitable components.

Figure 27:
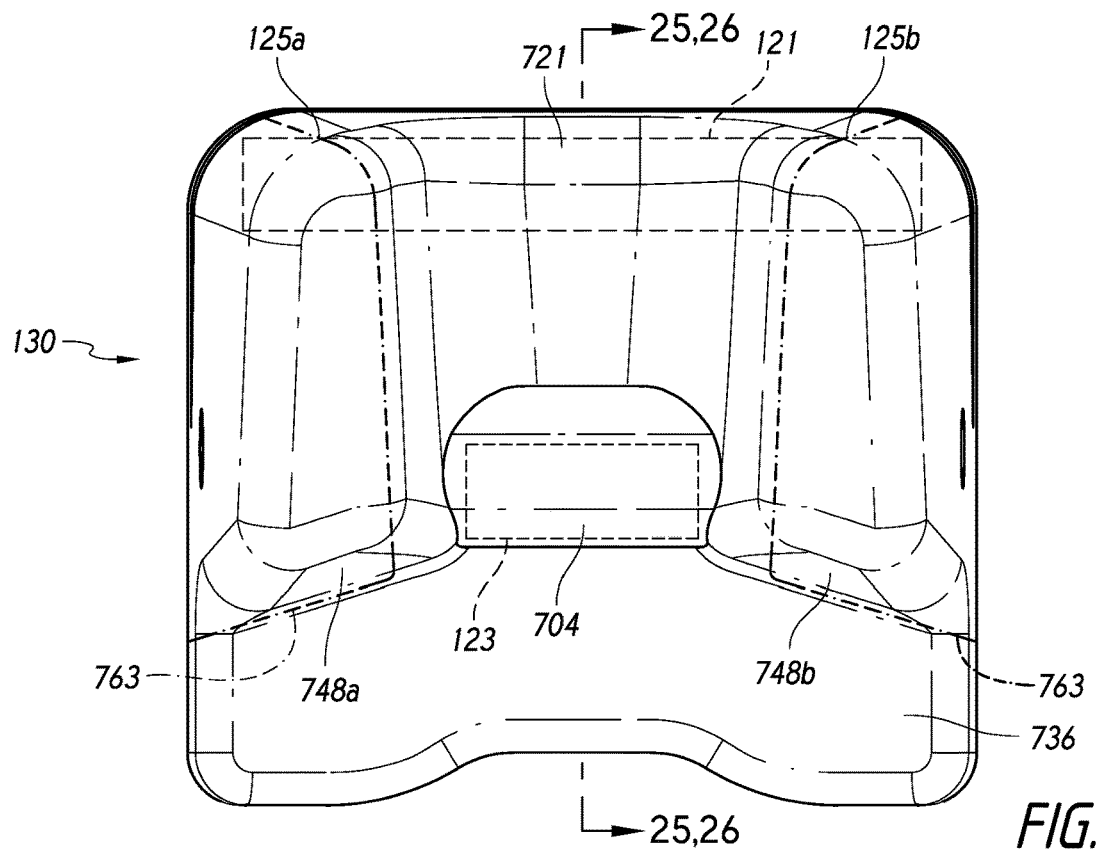
FIG. 27 is a top view of a pillow in accordance with embodiments of the present technology.

FIG. 25 is a cross-sectional view of the pillow 130 taken along line 25-25 of FIG. 27 when the pillow 130 is in an undeployed lowered configuration. FIG. 26 is a cross-sectional view of the pillow 130 taken along line 26-26 of FIG. 27 when the pillow 130 is in a deployed raised configuration. Referring now to FIG. 25, the pillow 130 includes an expandable opening 744 positioned generally under a region of a head-support surface 742 of the head cradle portion 702. A deployable member 121 can be positioned in the expandable opening 744 and can be deployed (e.g., expanded, inflated, etc.) to move the head cradle portion 702. A flexible region or joint 743 can connect the head cradle portion 702 to the base 709. In some embodiments, the head cradle portion 702 can be rotated an angle ? when the expandable member 121 moves from an unexpanded configuration (FIG. 25) to an expanded configuration (FIG. 26). The angle ? can be greater than or equal to about 5 degrees, about 10 degrees, about 20 degrees, about 30 degrees, about 40 degrees, about 50 degrees, or about 60 degrees to rotate the support surface 742 a corresponding angle. The amount of movement of the head cradle portion 702 can be selected based on the desired amount of head tilt.

FIG. 25 shows the neck support portion 704 positioned generally between the head cradle portion 702 and the shoulder support region 736. When the subject's head is supported by the head cradle portion 702, the neck support portion 704 is located under the subject's neck. A flexible portion or joint 747 can connect the neck support portion 704 to the base 709. An expandable opening 754 is located under the neck support portion 704. In some embodiments, an expandable member 123 can be inflated to push the neck support portion 704 upwardly to define an angle ? that is greater than or equal to about 5 degrees, about 10 degrees, about 15 degrees, about 20 degrees, about 25 degrees, about 30 degrees, about 35 degrees, about 40 degrees, or about 45 degrees to rotate the neck support portion 704 a corresponding angle. The amount of movement of the neck support portion 704 can be selected based on the desired support for the subject's neck.

The pillow 130 can include other types of movable features, such as movable panels (e.g., rotatable panels, linearly movable panels, etc.) or other features capable of being moved (e.g., translated, rotated, or both) to support, move, and/or otherwise interact with the subject's body. By way of example, the side portions 125 (FIG. 24) can include surfaces or features that move inward firmly to hold the patient's head. The number, locations, and properties (e.g., cushioning properties, breathability, etc.) of the movable features can be selected based on, for example, desired patient comfort, body positioning, and/or treatment parameters.

FIG. 27 is a top view of the pillow 130. The neck support portion 704 extends between shoulder-engagement ends 748a, 748b of the side portions 125a, 125b, respectively. The shoulder support region 736 is positioned to support the subject's shoulders when the shoulder-engagement ends 748a, 748b bear against the subject's right and left shoulders, respectively. The side portions 125a, 125b can include fasteners or other components for coupling to restraints (e.g., restraints 111a, 111b of FIG. 1). In some embodiments, the side portions 125a, 125b include hook or loop fasteners 763 (illustrated in dash-dot lines) for coupling to loop or hook fasteners of the restraints 111. For example, the fastener 763 can be sections of hook Velcro® closure. In other embodiments, the fastener 763 can include, without limitation, one or more snaps, buttons, ties, or other attachment features. Other regions of the pillow 130 can be made of breathable material and can have one-way or two-way stretchability.

Figure 28:
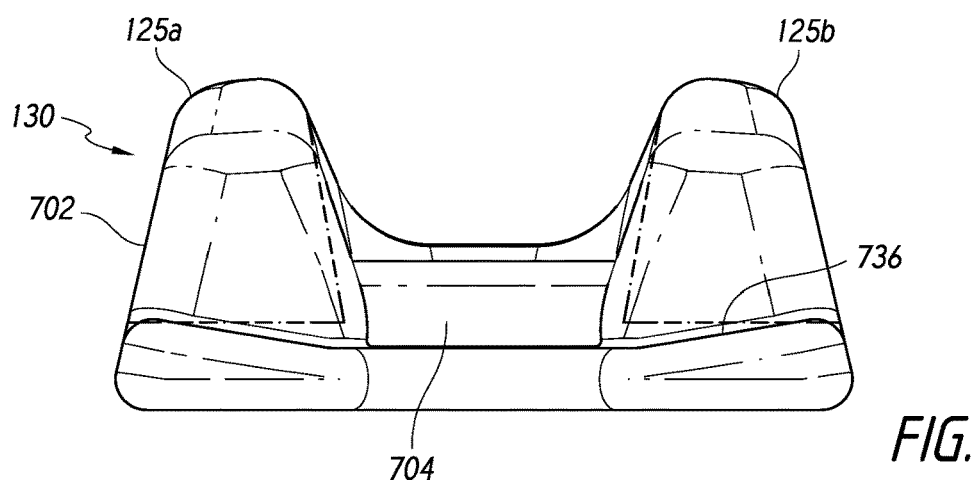
FIG. 28 is a front view of the pillow of FIG. 27.

FIG. 28 is a front view of the pillow 130 with the head cradle portion 702 having a substantially U-shaped profile (including V-shaped). The head cradle portion 702 can also have a semi-circular shape profile or other suitable shape for accommodating the subject's head. The heights of the side portions 125a, 125b can be selected such that the side portions 125a, 125b extend upwardly along opposite sides of the subject's head sufficient distances to reduce or limit side-to-side rotation of the subject's head.

Figure 29:
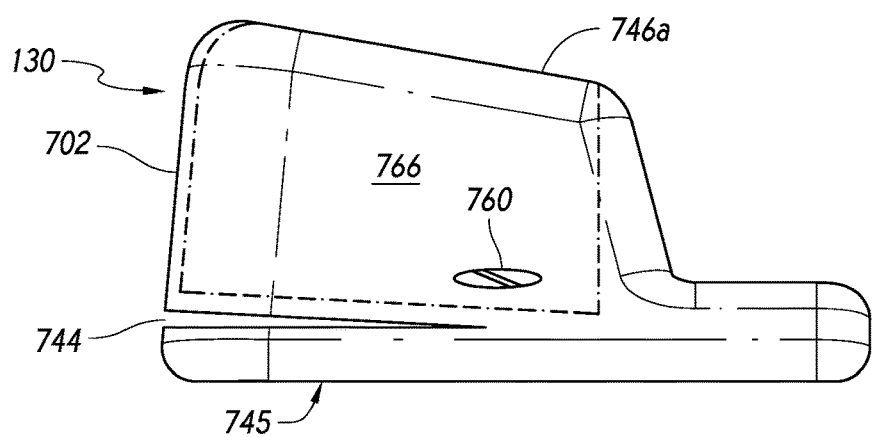
FIG. 29 is a side view of the pillow of FIG. 27.

FIG. 29 is a side view of the pillow 130. The expandable opening 744 can be a slot or a slit extending inwardly and generally parallel to a bottom surface 745 of the pillow 130. An access feature 760 in the form of a through-hole extends from an exterior surface 766 of the side portion 125a to the expandable opening 754 (FIGS. 25 and 26). The bottom surface 745 can comprise non-skid material for inhibiting movement of the pillow 130 along a support surface.

The pillow 130 can be made, in whole or in part, of a compressible material, including without limitation open-cell foam, closed-cell foam, or other compliant material. In some embodiments, the pillow 130 can be made of open-cell polyurethane foam. In some embodiments, the pillow 130 can include a cover for surrounding the foam main body. The cover can be removed and washed to provide a clean surface, and the cover can include fasteners (e.g., loop fastener, snaps, etc.) for coupling to restraints or other components.

Figure 30:
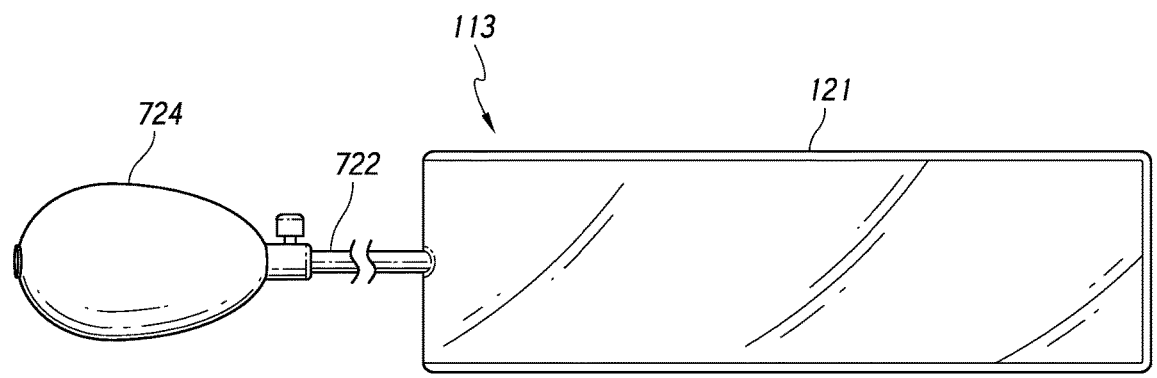
FIGS. 30 and 31 are top views of adjuster devices in accordance with embodiments of the present technology.

FIG. 30 is a top view of the head adjuster device 113. The pump 724 can be a bulb pump, a squeeze pump, or other manual pump and may include a button for releasing air. In other embodiments, the pump 724 is a motorized pump. The conduit 722 can be flexible tubing that fluidically couples the pump 724 to the expandable member 121. The expandable member 121 can comprise, in whole or in part, urethane, silicon, rubber, or other suitable material. Referring now to FIG. 27, the expandable member 121 (shown in phantom line) can be an inflatable bladder that extends across most of the width of the pillow 130.

Figure 31:
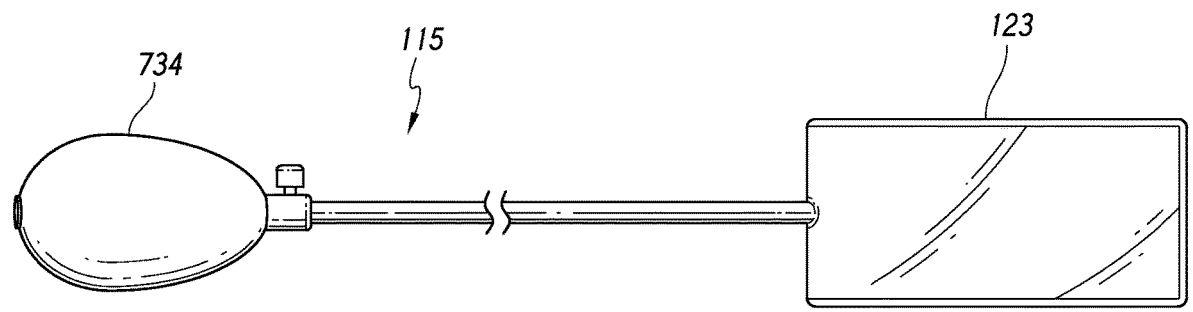

FIG. 31 is a top view of the neck adjuster device 115 generally similar to the head adjuster device 113 of FIG. 30 except as detailed below. The expandable member 123 can comprise urethane, silicon, rubber, or other suitable material and can be dimensioned to be located under the neck support portion 704. Referring now to FIG. 27, the expandable member 123 (shown in phantom line) is located generally between the side portions 125.

Figure 32:
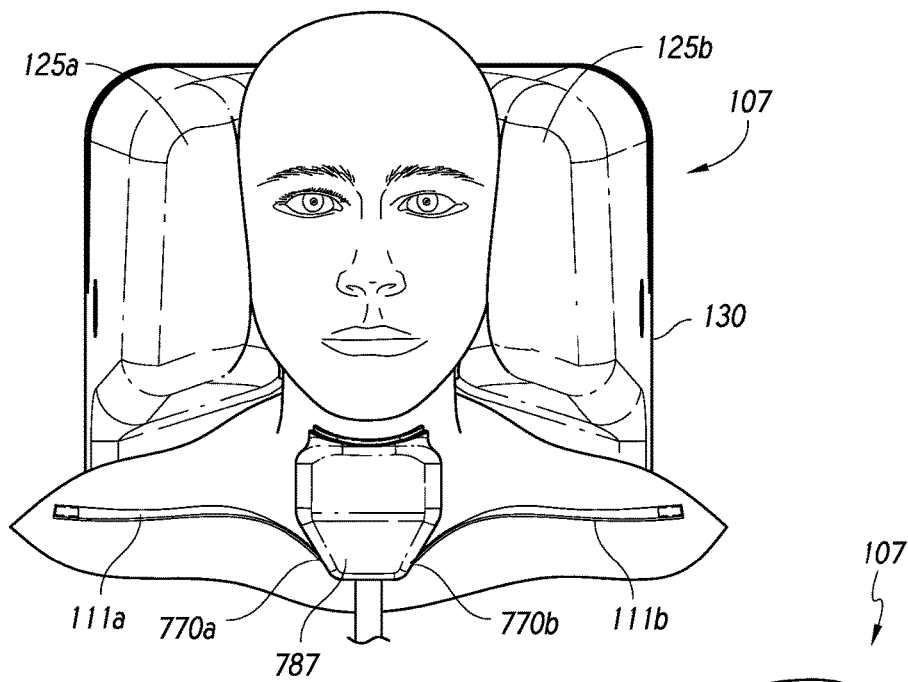
FIG. 32 is a top view of an adjustable pillow supporting the subject's head and restraints ready to be coupled to the pillow.
Figure 33:
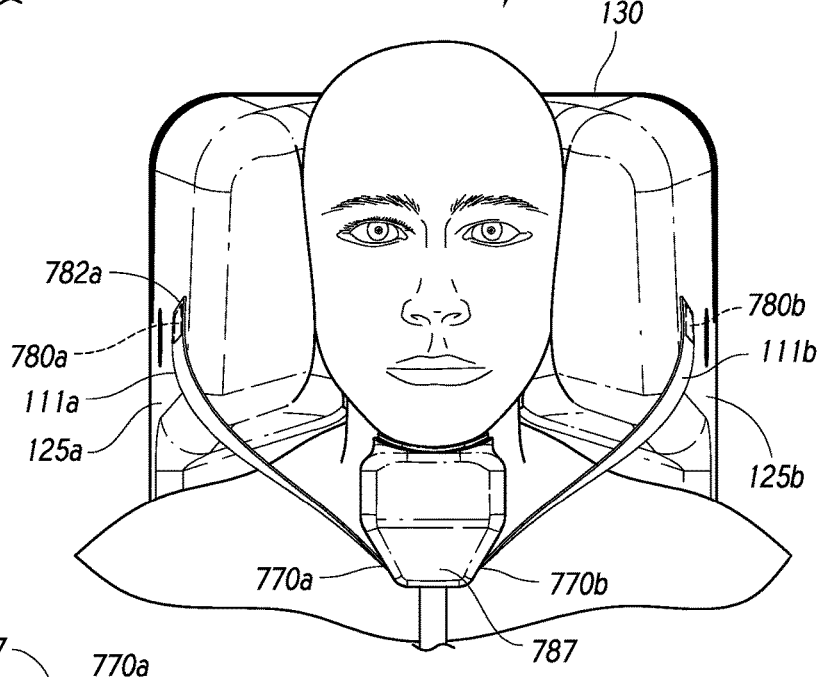
FIG. 33 is a top view of the restraint apparatus holding the applicator in thermal contact with the subject.
Figure 34:
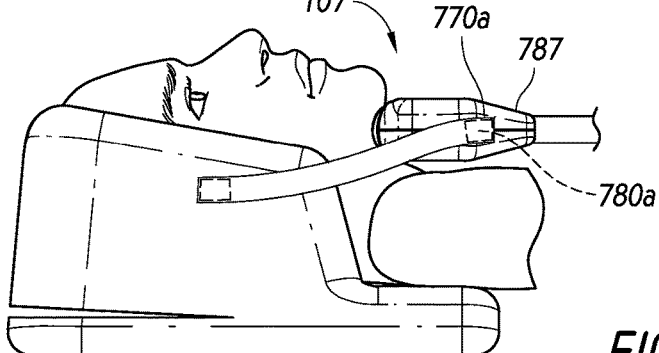
FIG. 34 is a side view of the restraint apparatus holding the applicator in thermal contact with the subject.

FIGS. 32-34 are a series of views of a method of performing cryotherapy using the restraint apparatus 107 in accordance with various embodiments of the present technology. Generally, the subject's head 109 can be positioned in the head cradle portion 702. An applicator 787 can then be aligned with the treatment site. The restraints 111a, 111b can be coupled to the side portions 125a, 125b and tensioned to pull the applicator 787 against the subject's submental region. After completing the treatment session, the restraints 111a, 111b can be detached from the respective side portions 125a, 125b to release the subject. Various details of operation are discussed in detail below.

FIG. 32 is a top view of the pillow 130 supporting the subject's head and restraints 111a, 111b ready to be coupled to the pillow. The restraints 111a, 111b can be straps permanently or detachably coupled to an applicator 787. For example, ends 770a, 770b of the respective restraints 111a, 111b can include hook or loop fasteners, snaps, ties, and/or other features for coupling to the applicator 787. In other embodiments, the restraints 111a, 111b can be part of a harness system with a harness body holding the applicator 787. The number, lengths, and configurations of the restraints 111a, 111b can be selected based on the location of the treatment site, desired force for holding the applicator 787, or other treatment parameters.

FIG. 33 is a top view of the restraint apparatus 107 holding the applicator 787 in thermal contact with the subject after fasteners 780a, 780b (illustrated in phantom line) of the restraints 111a, 111b have been applied to the pillow 130. The fasteners 780a, 780b can be loop fasteners located at or proximate to respective restraint ends 782a, 782b. Tensioning of the restraints 111, illustrated in a V arrangement, can be adjusted to inhibit or limit side-to-side movement of the applicator 787 and to stabilize the applicator 787 even if the subject's head moves slightly. During a single treatment session, the ends 782a, 782b can be coupled at various locations along the pillow 130 at different times, thus providing treatment flexibility.

FIG. 34 is a left side view of the restraint apparatus 107 holding the applicator 787 in thermal contact with the subject. Referring to FIGS. 33 and 34, the restraint ends 770a, 770b can be permanently or detachably coupled to the applicator 787. For example, the restraint end 770a can include a fastener 787a (e.g., a loop fastener shown in phantom line in FIG. 34) coupled to hook fastener of the applicator 787. The restraint ends 770 can be repositioned any number of times along the applicator 787. In other embodiments, the restraint ends 770 can be integrated into or part of the applicator 787, which can be similar or identical to the any of the applicators disclosed herein. The connection between the restraints 111 and the applicator 787 can be selected based on the design of the applicator.

H. Computing Environments

FIG. 35 is a schematic block diagram illustrating subcomponents of a controller in accordance with an embodiment of the disclosure. The controller can be part of the control module 106 (FIG. 1). For example, the controller 790 can be the controller 114 of FIG. 1 or can be incorporated into the applicators or other components disclosed herein. The controller 790 can include a computing device 800 having a processor 801, a memory 802, input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 35, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via the one or more input devices, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors and/or other data sources, and the output module 814 can communicate operator input to external computing devices and control variables to the controller. The display module 816 can be configured to convert and transmit processing parameters, sensor readings 818, output signals 820, input data, treatment profiles and prescribed operational parameters through one or more connected display devices, such as a display screen 118 (FIG. 1), printer, speaker system, etc.

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation. In various embodiments, the memory 802 can be flash memory, secure serial EEPROM, secure field programmable gate array, or secure application-specific integrated circuit. The memory 802 can store instructions for causing the applicators to cool/heat tissue, pressurization devices to draw a vacuum, or other acts disclosed herein. In one embodiment, the memory 802 stores instructions executable by the controller 790 for the thermal device to sufficiently cool conductive cups disclosed herein such that submental vacuum applicators non-invasively cool the subcutaneous lipid-rich cells to a desired temperature, such as a temperature less than about 0° C.

The input/output device 118 can include, without limitation, a touchscreen, a keyboard, a mouse, a stylus, a push button, a switch, a potentiometer, a scanner, an audio component such as a microphone, or any other device suitable for accepting user input and can also include one or more video monitor, a medium reader, an audio device such as a speaker, any combination thereof, and any other device or devices suitable for providing user feedback. For example, if an applicator moves an undesirable amount during a treatment session, the input/output device 803 can alert the subject and/or operator via an audible alarm. The input/output device 118 can be a touch screen that functions as both an input device and an output device. The control panel can include visual indicator devices or controls (e.g., indicator lights, numerical displays, etc.) and/or audio indicator devices or controls. The control panel may be a component separate from the input/output device 118 and/or output device 120, may be integrated applicators, may be partially integrated with one or more of the devices, may be in another location, and so on. In alternative embodiments, the controller 114 can be contained in, attached to, or integrated with the applicators. Further details with respect to components and/or operation of applicators, control modules (e.g., treatment units), and other components may be found in commonly-assigned U.S. Patent Publication No. 2008/0287839.

The controller 790 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

I. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above. While processes or acts are presented in a given order, alternative embodiments may perform the processes or acts in a different order, and some processes or acts may be modified, deleted, and/or moved. The headings provided herein are for convenience only and do not interpret the scope or meaning of the described technology.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

What is claimed is:

1. An apparatus for treating a subject's tissue, comprising:
    a thermally conductive cup including a first sidewall, a second sidewall, a first end wall, a second end wall, and a bottom, the bottom mechanically and thermally interconnects the first and second sidewalls such that cooling of only one of the sidewalls or the bottom results in the bottom, the first sidewall, and the second sidewall being similarly cooled;
    a lip having a first lip portion along the first sidewall and second lip portion along the second sidewall;
    a tissue-receiving cavity having a length between the first and second end walls, wherein the bottom of the thermally conductive cup, the first lip portion, and the second lip portion are each curved along the length of the tissue-receiving cavity such that the tissue-receiving cavity has a substantially uniform depth between the bottom and the lip along the length of the tissue-receiving cavity;
    at least one vacuum port in fluid communication with the tissue-receiving cavity to provide a vacuum for drawing the tissue into the tissue-receiving cavity, wherein the tissue-receiving cavity is sufficiently shallow to allow the subject's tissue to occupy substantially the entire tissue-receiving cavity when the vacuum is drawn via the at least one vacuum port; and
    a thermal device in thermal communication with only part of the conductive cup such that when the thermal element cools the part of the conductive cup the first sidewall, the second sidewall, and the bottom together cool an entire area of the subject's skin within the tissue-receiving cavity to non-invasively cool subcutaneous lipid-rich cells in the tissue an amount sufficient to be biologically effective in damaging and/or reducing the subcutaneous lipid-rich cells.

2. The apparatus of claim 1 wherein each of the first sidewall, the second sidewall, and the bottom is positioned to absorb heat from the tissue to damage and/or reduce the lipid-rich cells, which are in a subcutaneous layer of adipose tissue, in number and/or size to an extent while non-lipid-rich cells deeper than the subcutaneous layer of adipose tissue are not reduced in number and/or size to the extent.

3. The apparatus of claim 1, further comprising
    a pressurization device in fluid communication with the tissue-receiving cavity via the vacuum port; and
    a controller with instructions for causing the apparatus to hold the tissue in the tissue-receiving cavity using suction provided by the pressurization device while the conductive cup conductively cools the subject's tissue.

4. The apparatus of claim 1 wherein the conductive cup includes a metal surface that faces the tissue-receiving cavity and has an area equal to or less than about 40 cm$^2$.

5. The apparatus of claim 1, further comprising a restraint apparatus configured to hold a subject's head, wherein the restraint apparatus includes
    an adjustable pillow including a head cradle portion and being operable to controllably adjust tilt of the subject's head supported by the head cradle portion; and
    at least one restraint coupleable to the pillow such that the at least one restraint holds the conductive cup in thermal contact with the subject's region while the subject's head is supported by the head cradle portion.

6. The apparatus of claim 1, wherein the thermal device is operable to conductively cool all of the subject's epidermis within the tissue-receiving cavity and contacting the conductive cup, and wherein the first sidewall, the second sidewall, and the bottom each conductively cool the subject's epidermis while the vacuum is drawn.

7. The apparatus of claim 1, wherein the conductive cup is configured to define heat flow paths between the subject's skin in thermal contact with the conductive cup and the thermal device when the subject's tissue occupies substantially the entire tissue-receiving cavity.

8. The apparatus of claim 1, wherein the tissue-receiving cavity has a high thermal conductivity surface extending along the first sidewall, the second sidewall, and the bottom, the high thermal conductivity surface defining a substantially U-shaped transverse cross-sectional shape of the tissue-receiving cavity.

9. The apparatus of claim 1, wherein the tissue-receiving cavity has a substantially U-shaped transverse cross-sectional shape defining a maximum depth less than a transverse width at an entrance of the tissue-receiving cavity.

10. The apparatus of claim 1, wherein the thermally conductive cup is configured to conduct heat such that heat-exchanging surfaces of the bottom, the first sidewall, and the second sidewall are at ±3° C. of a target temperature, which is below −5° C., when the thermal device cools the thermally conductive cup.

11. The apparatus of claim 1, wherein the thermally conductive cup has a cooling area equal to or less than about 40 cm$^2$ and the tissue-receiving cavity has a depth less than about 5 cm.

12. The apparatus of claim 1, wherein the vacuum port extends through the first sidewall of the thermally conductive cup.

13. The apparatus of claim 1, wherein the at least one vacuum port includes at least one first vacuum port positioned along the first sidewall and at least one second vacuum port positioned along the second sidewall.

14. An apparatus for treating a subject's tissue, comprising:
    a vacuum applicator including
        a tissue-receiving cavity defined by a thermally conductive cup including a first sidewall, a second sidewall, a pair of end walls, and a bottom that mechanically and thermally interconnects the first and second sidewalls, wherein the tissue-receiving cavity has a length between the pair of end walls, and wherein the bottom is curved along the length of the tissue-receiving cavity,
        a contoured lip defining a mouth of the tissue-receiving cavity and including a first arcuate lip portion and a second arcuate lip portion, wherein the first and second arcuate lip portions are curved along the length of the tissue-receiving cavity, wherein the curvature of the bottom of the thermally conductive cup is same as the curvature of the first and second arcuate lip portions such that the tissue-receiving cavity has a substantially uniform depth between the bottom and the contoured lip along most of the length of the tissue-receiving cavity, wherein the contoured lip is configured to engage an area of the subject such that tissue of the subject extends through the mouth and fills substantially all of the tissue-receiving cavity while the vacuum applicator draws a vacuum and the first and second arcuate lip portions surround at least a portion of the subject's body, and a thermal device positioned to be in thermal contact with the tissue in the tissue-receiving cavity such that the thermal device is operable to cool the thermally conductive cup such that heat-exchanging surfaces of the first and second sidewalls and a bottom heat-exchanging surface, which connects the heat-exchanging surfaces of the first and second sidewalls, are at substantially the same temperature so as to cool substantially all of the subject's subcutaneous tissue located the tissue-receiving cavity to non-invasively cool subcutaneous lipid-rich cells in the tissue an amount sufficient to be biologically effective in damaging and/or reducing the subcutaneous lipid-rich cells.

15. The apparatus of claim 14, further comprising a controller with instructions for causing the thermal device to cool a conductive cup of the vacuum applicator such that the vacuum applicator non-invasively cools the subcutaneous lipid-rich cells to a temperature less than about 0° C.

16. The apparatus of claim 14, further comprising a vacuum source fluidically coupled to the tissue-receiving cavity and configured to provide sufficient vacuum to draw submental tissue of the subject to a bottom of the tissue-receiving cavity to bring the submental tissue into thermal contact with a concave metal heat-exchanging surface of the submental vacuum applicator.

17. The apparatus of claim 14 wherein the vacuum applicator includes an applicator unit and a liner assembly removably attached to the applicator unit.

18. A method of non-invasively cooling a target region of a subject, the method comprising:

placing an applicator on the subject, wherein the applicator includes a vacuum cup having a bottom and a lip, wherein the vacuum cup defines a tissue-receiving cavity having a longitudinal axis, and wherein the lip and the bottom are similarly curved along the longitudinal axis such that the tissue-receiving cavity has a substantially uniform depth between the lip and the bottom along the longitudinal axis;

drawing tissue through the tissue-receiving cavity and into thermal contact with a section of the vacuum cup located at a bottom of the tissue-receiving cavity; and conductively extracting heat from the tissue to the applicator to conductively cool substantially all of the subject's skin contacting the section of the vacuum cup located at the bottom of the tissue-receiving cavity and to conductively cool substantially all of the subject's skin contacting sidewalls of the vacuum cup such that an entire area of the vacuum cup thermally contacting the skin is at a temperature below −5 degrees C. so as to cool the subject's subcutaneous tissue an amount sufficient to be biologically effective in selectively damaging and/or reducing subcutaneous lipid-rich cells.

19. The method of claim 18 wherein conductively extracting heat from the tissue includes cooling submental tissue to cause damage to and/or reduction of a sufficient amount of the submental subcutaneous lipid-rich cells to visibly reduce a double chin of the subject.

20. The method of claim 18, further comprising supporting the subject's head on an adjustable pillow, wherein the adjustable pillow includes a deployable head cradle portion and is capable of controllably adjusting the forward tilt of a subject's head supported by the head cradle portion; and holding the applicator in thermal contact with a submental region of the subject using at least one restraint coupled to the pillow.

21. The method of claim 18, further comprising drawing at least one of a liner assembly, a cryoprotectant gel pad, and the tissue against the sidewalls of the vacuum cup.

22. The method of claim 21 wherein drawing at least one of the liner assembly, the cryoprotectant gel pad, and the tissue against the sidewalls of the vacuum cup includes generating vacuum pressure in the tissue-receiving cavity via one or more vacuum ports positioned along the sidewalls of the vacuum cup.

* * * * *